US007061622B2

(12) United States Patent
Rollins et al.

(10) Patent No.: US 7,061,622 B2
(45) Date of Patent: Jun. 13, 2006

(54) ASPECTS OF BASIC OCT ENGINE TECHNOLOGIES FOR HIGH SPEED OPTICAL COHERENCE TOMOGRAPHY AND LIGHT SOURCE AND OTHER IMPROVEMENTS IN OPTICAL COHERENCE TOMOGRAPHY

(75) Inventors: Andrew M. Rollins, Highland Heights, OH (US); Joseph A. Izatt, Raleigh, NC (US); Volker Westphal, Hannover (DE); Siavash Yazdanfar, Durham, NC (US)

(73) Assignees: Case Western Reserve University, Cleveland, OH (US); University Hospitals of Cleveland, Cleveland, OH (US)

( * ) Notice: Subject to any disclaimer, the term of this patent is extended or adjusted under 35 U.S.C. 154(b) by 302 days.

(21) Appl. No.: 10/213,326

(22) Filed: Aug. 5, 2002

(65) Prior Publication Data

US 2003/0137669 A1 Jul. 24, 2003

Related U.S. Application Data

(60) Provisional application No. 60/310,080, filed on Aug. 3, 2001, provisional application No. 60/310,083, filed on Aug. 3, 2001.

(51) Int. Cl.
*G01B 9/02* (2006.01)
(52) U.S. Cl. .................................... 356/497
(58) Field of Classification Search .............. 356/477, 356/497, 479
See application file for complete search history.

(56) References Cited

U.S. PATENT DOCUMENTS 4,063,549 A 12/1977 Beretsky et al.

(Continued)

FOREIGN PATENT DOCUMENTS

EP 0 421 279 A1 4/1991

(Continued)

OTHER PUBLICATIONS

Everett M.J. et al:"Non-invasive Diagnosis Of Early Caries With Polarization Sensitive Optical Coherence Tomography", Proceedings of the SPIE, SPIE, Bellingham, VA, us, vol. 3593, Jan. 24, 1999, pp. 177-182, XP000931184, Chapter 3, pp. 178-179, Figure 1.

(Continued)

*Primary Examiner*—Hwa (Andrew) Lee
(74) *Attorney, Agent, or Firm*—Renner, Otto, Boisselle and Sklar, LLP

(57) ABSTRACT

An optical coherence tomography (OCT) system including an interferometer provides illuminating light along a first optical path to a sample and an optical delay line and collects light from the sample along a second optical path remitted at several scattering angles to a detector. In one embodiment, illuminating light is directed along a number of incident light paths through a focusing lens to a sample. The light paths and focusing lens are related to the sample and to both the incident light source and the detector. In another embodiment, a focusing system directs light to a location in the sample. A transmission grating or acousto-optic modulator directs light from the sample at an angle representative of the wavelength of the incident light on the transmission grating or acousto-optic modulator.

11 Claims, 22 Drawing Sheets

U.S. PATENT DOCUMENTS

| | | | |
|---|---|---|---|
| 4,458,683 A | | 7/1984 | Saito et al. |
| 5,158,090 A | | 10/1992 | Waldman et al. |
| 5,426,506 A | | 6/1995 | Ellingson et al. |
| 5,491,524 A | | 2/1996 | Hellmuth et al. |
| 5,496,305 A | | 3/1996 | Kittrell et al. |
| 5,555,087 A | * | 9/1996 | Miyagawa et al. ......... 356/485 |
| 5,746,738 A | | 5/1998 | Cleary et al. |
| 5,877,856 A | | 3/1999 | Fercher |
| 5,892,583 A | | 4/1999 | Li |
| 6,134,003 A | | 10/2000 | Tearney et al. |
| 6,181,411 B1 | * | 1/2001 | Harris et al. ............... 356/4.01 |
| 6,191,862 B1 | | 2/2001 | Swanson et al. |
| 6,486,948 B1 | * | 11/2002 | Zeng .......................... 356/301 |

FOREIGN PATENT DOCUMENTS

| | | |
|---|---|---|
| EP | 0 697 595 A1 | 2/1996 |
| WO | WO 99/22198 | 5/1999 |
| WO | WO0069333 A | 11/2000 |
| WO | WO 01/42735 A1 | 6/2001 |

OTHER PUBLICATIONS

Boer De J.F. et al: "Polarization Effects In Optical Coherence Tomography of Various Biological Tissues", IEEE Journal of Selected Topics in Quantum Electronics, IEEE Service Center, US., vol. 5, No. 4, Jul. 1999, pp. 1200-1203, XP00893469, Chapter III, pp. 1200-1201, Figure 1.

Podoleanu A.G. et al: "Simultaneous En-Face Imaging of Two Layers in the Human Retina by Low-Coherence Reflectometry", Optics Letters, Optical Society of America, Washington, US, vol. 22, No. 13, Jul. 1, 1997, pp. 1039-1041, XP000658709.

Podoleanu A.G. et al: "Simultaneous Low Coherence Interferometry Imaging at Two Depths Using an Integrated Optic Modulator", Optics Communications, North-Holland Publishing Co., Amsterdam, NL, vol. 191, No. 1-2, May 1, 2001, pp. 21-30 XP004234990.

* cited by examiner

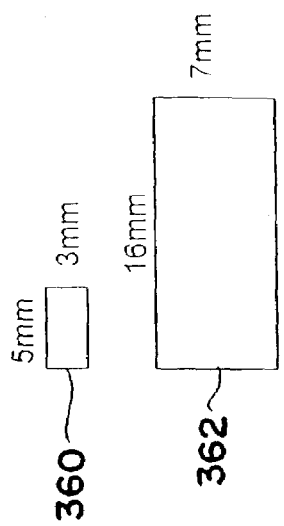
FIG. 22
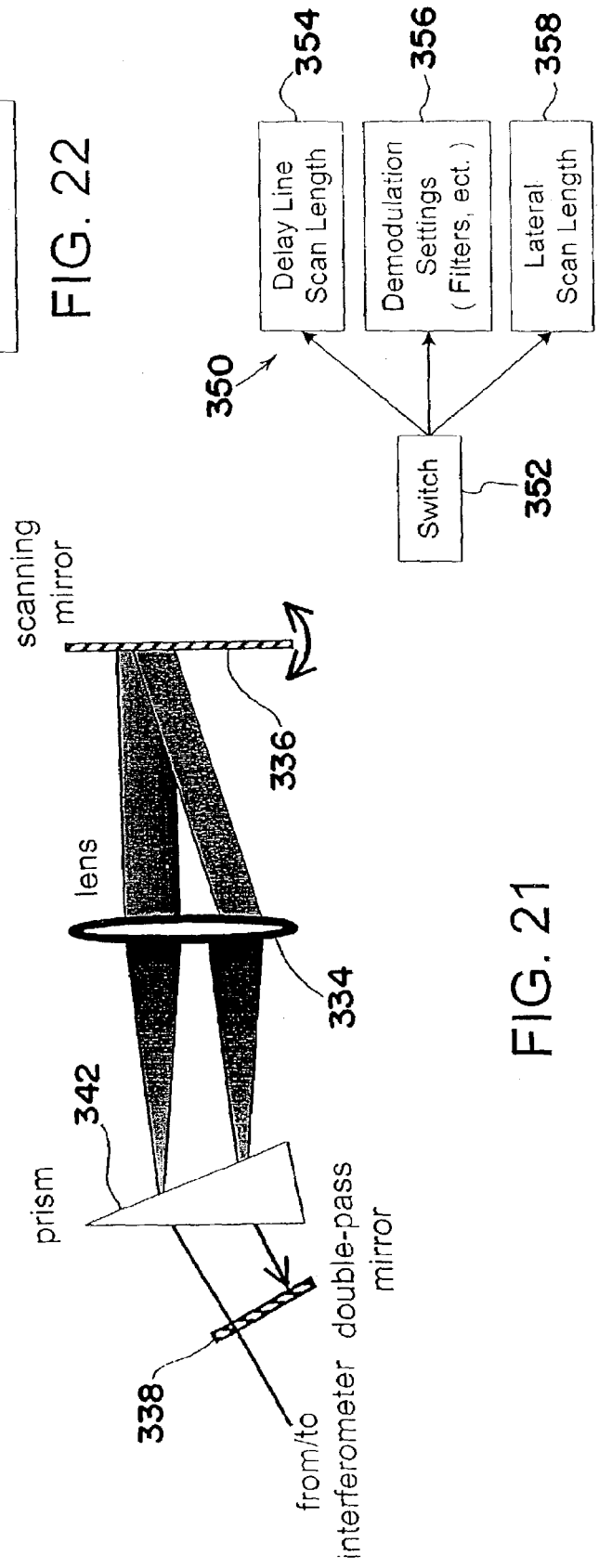
FIG. 23
FIG. 21

ASPECTS OF BASIC OCT ENGINE TECHNOLOGIES FOR HIGH SPEED OPTICAL COHERENCE TOMOGRAPHY AND LIGHT SOURCE AND OTHER IMPROVEMENTS IN OPTICAL COHERENCE TOMOGRAPHY

Applicants claim the benefit of U.S. Provisional Applications No. 60/310,080 and 60/310,083, both filed Aug. 3, 2001, the entire disclosures of which are hereby incorporated herein.

FIELD OF THE INVENTION

The present invention is directed to a real-time imaging system and method that is particularly useful in the medical field, and more particularly, to a system and method for imaging and analysis of tissue and other samples using optical coherence tomography.

BACKGROUND OF THE INVENTION

A variety of imaging techniques are used for the medical diagnosis and treatment of patients. Ultrasound imaging represents a prevalent technique. Ultrasound uses sound waves to obtain a cross-sectional image of an object. These waves are radiated by a transducer, directed into the tissues of a patient, and reflected from the tissues. The transducer also operates as a receiver to receive the reflected waves and electronically process them for ultimate display.

Another imaging technique is referred to as Optical Coherence Tomography (OCT). OCT uses light to obtain a cross-sectional image of tissue. The use of light allows for faster scanning times than occurs in ultrasound technology. The depth of tissue scan in OCT is based on low coherence interferometry. Low coherence interferometry involves splitting a light beam from a low coherence light source into two beams, a sampling beam and a reference beam. These two beams are then used to form an interferometer. The sampling beam hits and penetrates the tissue, or other object, under measurement. The sampling or measurement beam is reflected or scattered from the tissue, carrying information about the reflecting points from the surface and the depth of tissue. The reference beam hits a reference reflector, such as, for example, a mirror or a diffraction grating, and reflects from the reference reflector. The reference reflector either moves or is designed such that the reflection occurs at different distances from the beam splitting point and returns at a different point in time or in space, which actually represents the depth of scan. The time for the reference beam to return represents the desirable depth of penetration of tissue by the sampling beam.

When the reflected beams meet, intensities from respective points with equal time delay form interference. A photodetector detects this interference and converts it into electrical signals. The signals are electronically processed and ultimately displayed, for example, on a computer screen or other monitor.

Optical coherence tomography (OCT) is a relatively new, non-invasive optical imaging technique. OCT is analogous in principle to pulse-echo ultrasound imaging, but near-infrared light waves instead of acoustic waves are employed to probe the sample specimen. OCT has been primarily applied to imaging of biological tissues, providing micron-scale resolution in three dimensions to a depth of a few millimeters without contacting the tissue. We here disclose a number of advanced designs and techniques that extend the utility of OCT and/or are based on OCT.

A number of papers and other references are cited below. These provide additional information and background concerning OCT, and they are incorporated by reference.

A number of features and embodiments are disclosed below; and it will be appreciated that the features may be combined and/or substituted for each other.

BRIEF DESCRIPTION OF THE DRAWINGS

FIG. 21 is a schematic illustration of a RSOD line including prism in accordance with an alternative embodiment of the present invention;

FIG. 22 is a schematic illustration of images resulting from two different scan depths;

FIG. 23 is a schematic illustration of a switchable amplitude adjustment subsystem in accordance with the present invention;

SUMMARY

Figure 1:
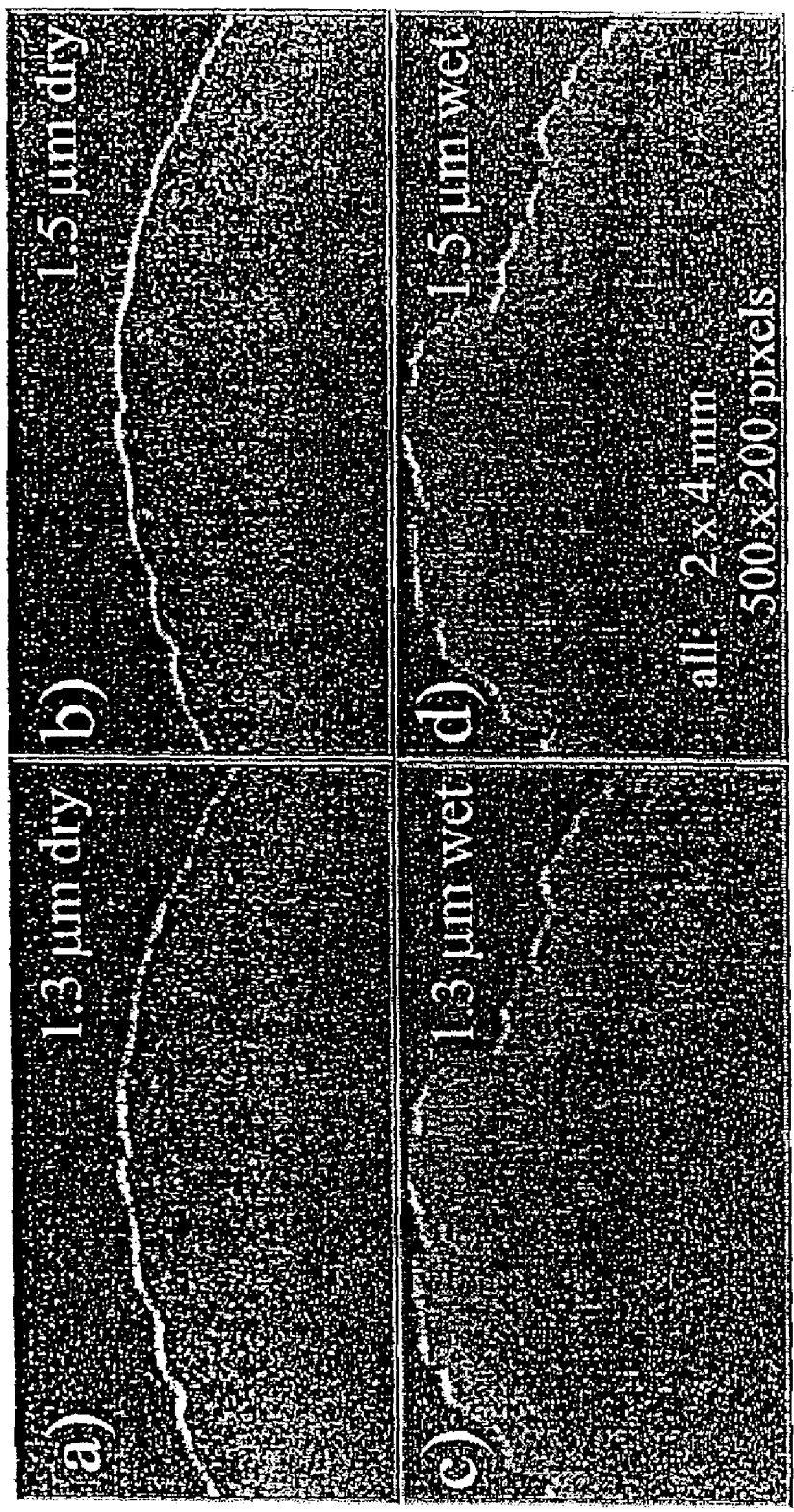
FIG. 1 illustrates OCT images of in vivo human skin.

In accordance with one aspect of the present invention, a transformation device for an OCT (optical coherence tomography) system in which double sided scanning is carried out includes plural buffers, one for data obtained during the forward scan by the OCT system and another for data obtained during the reverse scan by the OCT system. One of the buffers is first in first out (FIFO) type and a different one of the buffers is first in last out (FILO) type.

In accordance with another aspect of the present invention, an OCT system includes an interferometer and an optical delay line, wherein the optical delay line includes a transmissive optically dispersive device.

In accordance with another aspect of the present invention, an OCT system includes an imaging system to obtain information of a sample and a control to control the imaging system to obtain images at discrete number of depths in the sample.

In accordance with another aspect of the present invention, a method of preserving signal to noise ratio in the case of nonlinear scan rate in operation of an OCT system includes generating a local oscillator signal with a frequency that varies as the center frequency of the OCT signal varies and demodulating the time-varying OCT signal to a fixed intermediate frequency or to DC. In accordance with another aspect of the present invention, an OCT system includes an interferometer, and is characterized in that the interferometer has an optical path to bring light to a sample and a separate optical path from the sample to a detector.

In accordance with yet another aspect of the present invention, a method of approximating an optical circulator in an OCT system having an interferometer includes directing light via a first optical path to a sample, directing light from the sample via a second optical path to a detector, and detecting light from the sample and from an optical delay line.

In accordance with yet another aspect of the present invention, a device for simultaneously collecting light from a sample remitted at several scattering angles includes a reflector having a surface positioned relative to the sample to receive light scattered from a location of the sample at different respective scattering angles and a collection lens for collecting such scattered light and directing it to the reflector.

In accordance with yet another aspect of the present invention, a device for simultaneously illuminating and collecting light from a sample remitted at several scattering angles includes a fiber optic member for illuminating the sample, and a group of fiber optic members arranged relative to the illuminating fiber optic member to collect light scatted at respective scattering angles by the sample.

In accordance with yet another aspect of the present invention, an interferometer includes a low coherence source and a beamsplitter for directing light from the source to a sample and to a reference optical delay line. A scanning system scans a sample with the incident light from the source and a detector system detects light scattered by the sample at multiple angles.

In accordance with yet another aspect of the present invention, a device for simultaneously illuminating and collecting light from a sample remitted at several scattering angles includes a number of incident light paths and a focusing lens for directing light from such light paths to a common spot of a sample. The light path and focusing lens are related to the sample and to both incident light source and detector for directing light remitted at several angles from the sample to the detector along at least part of the incident light paths.

In accordance with yet another aspect of the present invention, a system for illuminating a sample and for receiving light from the sample for analysis includes a focusing system for directing light to a location in the sample and a light path for scattered light from the sample. A transmission grating directs light from the sample at an angle representative of the wavelength of the incident light on the transmission grating.

In accordance with yet another aspect of the present invention, an interferometer system includes at least two light sources and a combiner for combining light from the two light sources. The system further includes sample and optical delay line light paths, and a detector for detecting light from both the sample and delay line light paths.

DETAILED DESCRIPTION OF THE INVENTION

1 Spectroscopic OCT

Spectroscopic OCT can be defined as a family of techniques using OCT to measure optical properties of a sample system as a function of wavelength. Methods to perform absorption spectroscopy and elastic scattering spectroscopy with depth resolution using OCT have been proposed and, to some extent, demonstrated (See M. D. Kulkarni and J. A. Izatt, "Spectroscopic Optical Coherence Tomography," presented at Conference on Lasers and Electro-Optics, 1996, and U. Morgner, "Spectroscopic Optical Coherence Tomography," presented at Conference on Lasers and Electro-Optics Technical Digest, Baltimore, Md., 1999, which are incorporated by reference).

This field of OCT research has not been extensively explored and represents one of the most fruitful avenues of investigation in OCT.

1.1 Wavelength Ratiometric OCT

The technique of wavelength-ratiometric OCT (WROCT) is a relatively simple spectroscopic OCT method that holds the potential to produce images using analyte concentration as contrast. WROCT can be used to image analyte concentration based on the differential absorption of two wavelengths. The intensity of the signal of wavelength λ backscattered from a depth x in an approximately homogenous medium can be expressed as:

$$S(\lambda, x) = B(x) I(\lambda, 0) e^{-2x(\mu_a(\lambda) + \mu_s)} \quad (6.1)$$

where B(x) is the backscatter profile of the sample medium, related to the probability that a singly scattered photon will be collected by the OCT probe fiber. $I(\lambda, 0)$ is the intensity of the incident beam, and $\mu_a$ and $\mu_s$ are the attenuation and scattering coefficients respectively. The two wavelengths should be chosen such that the scattering coefficients are approximately equal and the attenuation coefficients are as different as possible. Under these assumptions, and using incident beams of equal intensity, the natural logarithm of the ratio of the signals at two wavelengths is:

$$\ln\left(\frac{S(\lambda_1, x)}{S(\lambda_2, x)}\right) = 2xC(\sigma_a(\lambda_2) - \sigma_a(\lambda_1)) \quad (6.2)$$

where C is the concentration of the absorber and $\sigma_a(\lambda)$ is the absorption cross section of the absorber at wavelength λ. Therefore, the natural logarithm of the ratio of the signals at two wavelengths is proportional to the concentration of the absorber.

Light from both sources can be coupled into the OCT interferometer at the same time using a wavelength division multiplexer (WDM) or a dichroic mirror. The two images can be separated by demodulating the detected interferometric signal from the scanning reference mirror at the different Doppler shift frequencies corresponding to the different wavelengths. This technique for simultaneous dual-wavelength OCT has been demonstrated previously (See G. Gelikonov, V. Gelikonov, F. Feldchtein, J. Stepanov, A. Sergeev, I. Antoniou, J. Ionnovich, D. Reitze, and W. Dawson, "Two-Color-In-One-Interferometer OCT System For Bioimaging," presented at Conference on Lasers and Electro-Optics, 1997, which is incorporated by reference).

1.1.1 Imaging Water Concentration

We have implemented a dual-wavelength OCT system and have demonstrated it by imaging phantoms and in vivo skin at two wavelengths simultaneously. (Phantoms may be, for example, samples representing characteristics of skin, although other samples may be examined, tested or the like using the several methods and devices disclosed herein.

For imaging water concentration, we chose 1.3 μm and 1.55 μm as our two wavelengths because the absorption coefficients of tissue (primarily due to water) at these wavelengths are different by an order of magnitude, the scattering coefficients of tissue at these two wavelengths are approximately equal, and because low coherence sources are readily available at these wavelengths. Differential absorption of 1.3 μm light and 1.55 μm light was observed as a function of water concentration. In addition, we have developed a more suitable algorithm for reconstructing spatially resolved maps of analyte concentration from simultaneously acquired OCT images at different wavelengths for which the optical properties of the analyte are known. It was found that simply calculating the ratio of the two OCT images was not sufficient because an OCT image maps the integrated attenuation of light as a function of depth. A more correct model is expressed by:

$$\int C(x) \partial x = \frac{\ln(R(x)) - \ln(I(\lambda_1)/I(\lambda_2))}{2(\sigma_a(\lambda_1) - \sigma_a(\lambda_2))}, \quad (6.3)$$

where C(x) is the analyte concentration as a function of imaging depth x, R(x) is the ratio of the data at the two imaging wavelengths $\lambda_1$ and $\lambda_2$, $I(\lambda_1)/I(\lambda_2)$ is the relative incident intensity, and $\sigma_a$ is the absorption coefficient. The scattering coefficient is assumed equal for the two wavelengths. The reconstruction algorithm for an analyte concentration map consists of filtering the images to equivalent spatial resolutions, thresholding above the noise floor, detecting the surface peaks for determination of relative incident intensity (if unknown), calculating the ratio and $\int C(x) \partial x$ for each A-scan, then differentiating each A-scan to generate values of analyte concentration as a function of depth.

FIG. 1 illustrates OCT images of in vivo human skin. Frames (a) and (b) were acquired simultaneously from dry skin using 1.3 μm and 1.55 μm light. Frames (c) and (d) were acquired identically from skin soaked in water. A stronger differential absorption is apparent in the wet skin than the dry skin due to a stronger absorption of 1.55 μm light than 1.3 μm light by water.

1.1.2 Imaging Oxygen Saturation

The recent development by Izatt and others of Color Doppler OCT (See J. A. Izatt and M. D. Kulkarni, "Doppler Flow Imaging Using Optical Coherence Tomography," in Conference on Lasers and Electro-Optics, vol. 9 of 1996 OSA Technical Digest Series. Washington, DC: Optical Society of America, 1996, pp. postdeadline paper CPD3-1, J. A. Izatt, M. D. Kulkarni, S. Yazdanfar, J. K. Barton, and A. J. Welch, "In Vivo Bidirectional Color Doppler Flow Imaging of Picoliter Blood Volumes Using Optical Coherence Tomography," Optics Letters, vol. 22, pp. 1439–1441, 1997, and Z. Chen, T. E. Milner, S. Srinivas, X. Wang, A. Malekafzali, M. J. C. v. Gemert, and J. S. Nelson, "Noninvasive imaging of in vivo blood flow velocity using optical Doppler tomography," Optics Letters, vol. 22, pp. 1119–1121, 1997, which are incorporated by reference) (see above) has increased the spatial resolution available for diagnostic blood flow monitoring by at least an order of magnitude over ultrasound techniques, with a commensurate increase in flow velocity estimation accuracy. However, flow measurements only peripherally address the relevant problem in most clinical situations, which is determination of tissue oxygen perfusion. A significant step toward closing this gap may be taken by developing spatially resolved blood oxygen saturation mapping using WROCT. We propose a simple extension of the well known technique of pulse oximetry, in which the blood oxygen saturation in a tissue volume is determined from the ratio of optical absorbance measurements performed at two wavelengths with differential absorption in oxy-and deoxy-hemoglobin (typically 650 and 805 nm) (See I. Yoshiya, Y. Shimada, and K. Tanaka, "Spectrophotometric Monitoring of Arterial Oxygen Saturation in the Fingertip," Med. Biol. Eng. & Comp., vol. 18, pp. 27–32, 1980, which is incorporated by reference). In pulse oximetry, the proportion of the optical absorption in the arterial blood volume is determined from the magnitude of absorbance changes as a function of the patient's pulse. In our proposed imaging extension of pulse oximetry, simultaneous OCT images will be taken at two wavelength regions with differential absorption in oxy- and deoxy-hemoglobin. This will be done by using two low-coherence sources at the appropriate wavelengths, for example 780 and 830 nm. Pulse variations will not be required for separating hemoglobin absorption from tissue absorption, as the absorbance data obtained using OCT will have intrinsic spatial resolution. If necessary, Doppler flow processing will be performed on either or both of the wavelength range image datasets in order to isolate blood vessels in the tissue.

The ideal wavelength range pair to use for dual-wavelength imaging will have differential absorption in hemoglobin, but similar scattering characteristics so that ratiometric variations can be attributed to blood oxygenation status. If present, global wavelength-dependent scattering variations could be corrected using image processing prior to oxygen saturation analysis.

To test the wavelength ratiometric oxygen saturation mapping concept in the laboratory, a phantom for circulation measurements could be developed consisting of a capillary-tube based blood flow system embedded in a polymer microsphere suspension. Potential clinical applications of this technique include evaluation of retinal perfusion in patients with suspected macular degeneration, and evaluation of the healing response following plastic surgery.

1.2 Spectroscopic OCT by Pathlength-Resolved Dispersion Measurement

It has been demonstrated that low coherence interferometry can be used to measure chromatic dispersion (See L. Thevenaz, J.-P. Pellaux, and J.-P. V. D. Weid, "All-Fiber Interferometer for Chromatic Dispersion Measurements," Journal of Lightwave Technology, vol. 6, pp. 1–7, 1988, P.-L. Francois, M. Monerie, C. Vassallo, Y. Durteste, and F. R. Alard, "Three Ways to Implement Interferencial Techniques: Application to Measurements of Chromatic Dispersion, Birefringence, and Nonlinear Susceptibilities," Journal of Lightwave Technology, vol. 7, pp. 500–513, 1989, T. Hellmuth and M. Welle, "Simultaneous Measurement of Dispersion, Spectrum, and Distance With a Fourier Transform Spectrometer," Journal of Biomedical Optics, vol. 3, pp. 7–11, 1998, and S. D. Dyer and K. B. Rochford, "Low-coherence interferometric measurements of fibre Bragg grating dispersion," Electronics Letters, vol. 35, pp. 1485–1486, 1999, which are incorporated by reference).

This is based on the principle that although the autocorrelation of an optical source is insensitive to the spectral phase, a cross-correlation measurement is sensitive to the spectral phase difference between the sample and reference fields. Since the sample and reference fields originate from the same source, the spectral phase difference can be attributed to the chromatic dispersion mismatch between the sample and reference arms of the measurement interferometer. Thus, if a Fourier transform spectrometer is modified to put the sample in one of the interferometer arms, then a cross-correlation is measured and the resulting interferogram will have information related to the dispersion of the sample. Specifically, the phase of the Fourier transform of the interferogram should be proportional to the chromatic dispersion mismatch. OCT is fundamentally a cross-correlation measurement, so it naturally lends itself to this application. The applications of measuring dispersion in biological samples has not been explored thoroughly. One example of a potential application is the measurement of an analyte of interest (such as glucose) in a medium whose dispersion properties might be expected to change as a function of the analyte concentration (such as the aqueous humor of the eye).

It is also well known that dispersion (wavelength dependent refractive index) and wavelength dependent absorption are related by the Kramers-Kronig relations:

$$\chi'(v) = \frac{2}{\pi} \int_0^\infty \frac{s\chi''(s)}{s^2 - v^2} ds \qquad (6.4)$$

$$\chi''(v) = \frac{2}{\pi} \int_0^\infty \frac{v\chi'(s)}{v^2 - s^2} ds, \qquad (6.5)$$

where $\chi'$ and $\chi''$ are the real and imaginary parts of the complex susceptibility of the material, respectively, and v is the optical frequency. This relationship arises from a systems theory approach to the response of the polarization density P(t) in a material to an applied electric field E(t). A linear, shift-invariant system with a transfer function proportional to the susceptibility $\chi(\mu)$ relates the output, P(t), to the input E(t). Because the system is causal, the impulse response is asymmetrical, so the transfer function, and $\chi(v)$ must be complex, with real and imaginary parts related by the Hilbert transform pair. Since E(t) and P(t) are real, the impulse response must be real. Therefore the complex susceptibility must be symmetrical, $\chi(-v)=\chi^*(v)$, and obey the Kramers-Kronig relations (6.4) and (6.5) (See B. E. A. Saleh and M. C. Teich, Fundimentals of Photonics, New York, N.Y.: John Wiley & Sons, Inc., 1991, which is incorporated by reference). The index of refraction n and the absorption coefficient α of the material are related to the complex susceptibility by:

$$n - j\frac{a}{2k_0} = \sqrt{1 + \chi' + j\chi''} \qquad (6.6)$$

where $k_0$ is the free-space wavenumber. For a weakly absorbing medium (small $\chi'$ and $\chi''$), the refractive index and the absorption coefficient can be approximated as:

$$n \approx 1 + \frac{1}{2}\chi', \text{and} \qquad (6.7)$$

$$\alpha \approx -k_o \chi''. \qquad (6.8)$$

Thus, using OCT to measure an interferometric cross-correlation of the field reflected from a sample and the reference field, the wavelength-dependent index of refraction can be measured by calculating the phase of the Fourier transform of the interferogram. Then, by applying equation (6.7), then (6.5), then (6.8), the absorption spectrum can be calculated. It is hoped that by measuring the absorption spectrum in this way, in addition to directly measuring the attenuation (absorption and scattering) spectrum, that absorption and scattering effects can be separated. This could be useful because absorption should relate to the composition of the sample (e.g. analyte concentration), while scattering properties should relate to the structure of the sample(e.g. particle sizes).

2 Specialized Alternative Fiber Interferometers

The fiber-optic Michelson interferometer has been the most common configuration for OCT since the beginning of the field. This design is not optimum and more specialized interferometers are needed in order to improve sensitivity.

This section illustrates a number of additional interferometer configurations which may be useful for OCT under special conditions. Because of the significant advantages of using optical fibers to guide the light in an OCT interferometer, this discussion will be restricted to fiber interferometers, as opposed to bulk, free-space interferometers, although the invention also may be used equivalently in the latter.

2.1 Transmissive Samples

Figure 2A:
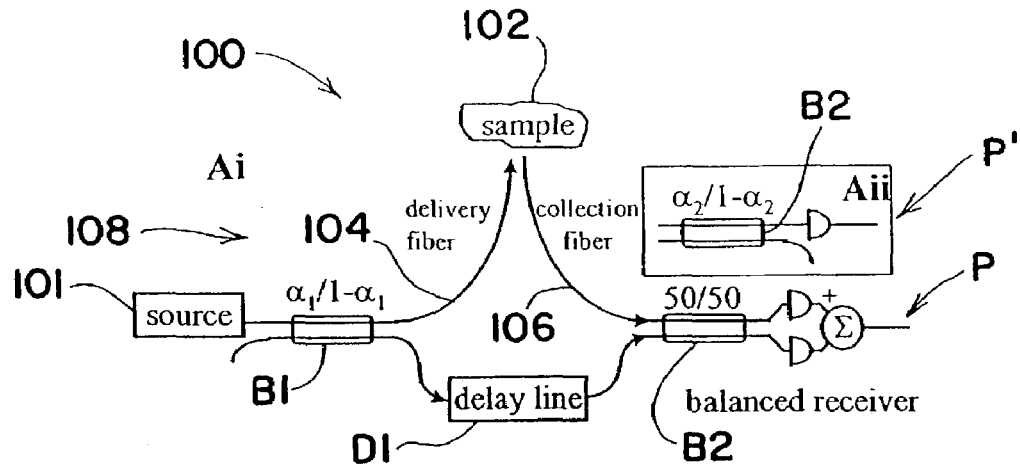
FIG. 2A is a schematic illustration of a transmissive Mach-Zehnder interferometer in accordance with one embodiment of the present invention.
Figure 2B:
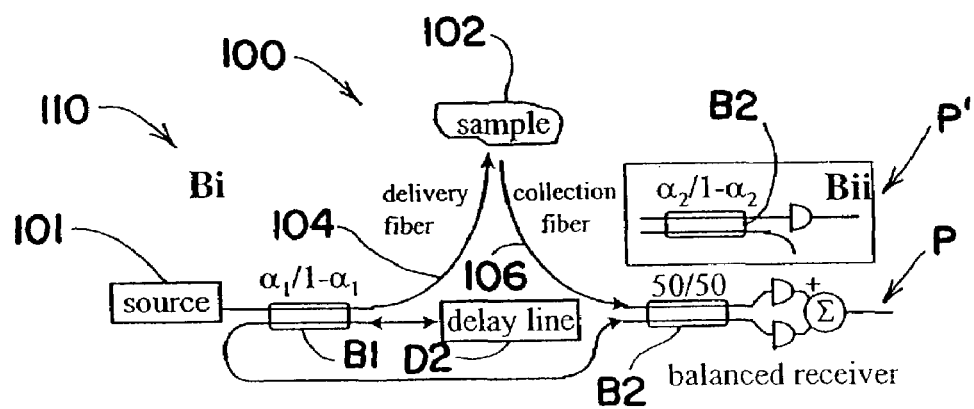
FIG. 2B is a schematic illustration of a transmissive Mach-Zehnder interferometer in accordance with an alternative embodiment of the present invention.

Here in FIG. 2A, transmissive will be taken to mean that the probe light 100 from source 101 is delivered to the sample 102 and collected from the sample with separate optics, specifically, separate fibers 104, 106. FIGS. 2A, 2B illustrate the Mach-Zehnder interferometer 108, 110 designs adapted for transmission rather than reflection.

(Mach-Zehnder interferometers are known, as several of the references cited herein describe. For example, low coherence light from light source 101 provides light to a beamsplitter B1 that has a "splitting ratio" alpha α1/(1-alpha α1, that directs light to a sample 102 and to a delay line D1 (transmissive delay line), D2 (reflective delay line). Light from the sample and light from the delay line are combined in a beamsplitter B2, which may be balanced as a 50/50 splitting ratio for directing light to a differential detector P, or which may have a different splitting ration and directs light to a detector P'), as is represented at the fragmentary inserts in FIGS. 2A and 2B.)

Figure 3A:
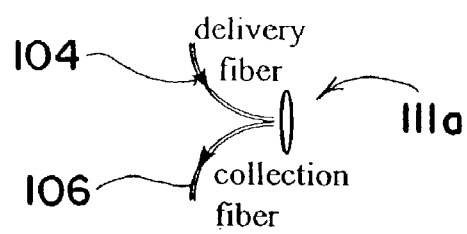
FIGS. 3A–3C are schematic illustrations of alternative orientations of delivery and collection fibers for use in conjunction with the present invention.
Figure 3B:
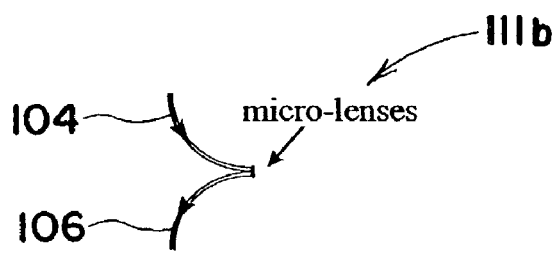
Figure 3C:
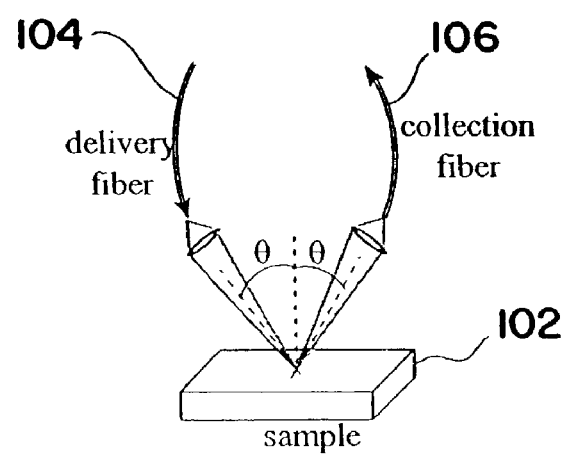

These interferometers can be used with the delivery and collection fibers 104, 106 in any arbitrary orientation with respect to each other and the sample 102. For example, the fibers could be placed exactly next to each other, and even use the same focusing optics (111a, 111b in FIGS. 3A, 3B) in order to approximate the operation of an optical circulator for collecting sample light to a different path than the path from which it was delivered, as illustrated in FIG. 3A, 3B. Alternatively, the collection fiber 106 can be at a distinct angle from the delivery fiber 104 (FIG. 3C), perhaps in order to measure backscatter as a function of angle, as described in section 3 below. Or these configurations could be used in a transillumination mode, with the collection fiber 106 oriented to collect light that passes through the sample 102 from the delivery fiber 104. In fact, the configuration labeled 110 in FIG. 2B has been used for a transillumination measurement (See M. R. Hee, J. A. Izatt, J. M. Jacobson, E. A. Swanson, and J. G. Fujimoto, "Femtosecond Transillumination Optical Coherence Tomography," Opt. Lett., vol. 18, pp. 950, 1993, which is incorporated by reference).

2.2 Spatially Multiplexed Signal Collection

Figure 4:
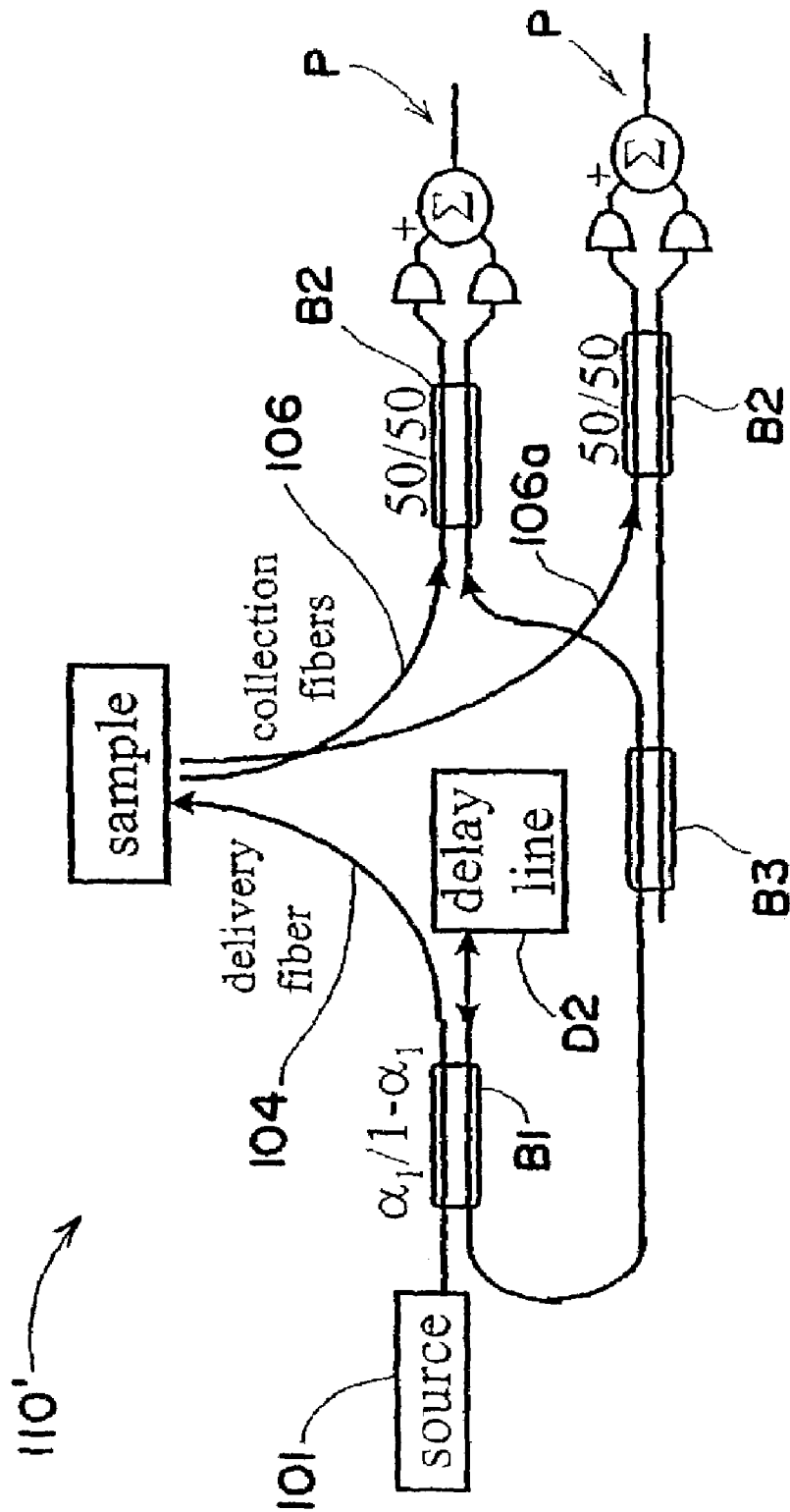
FIG. 4 is a schematic illustration of an alternative embodiment of the interferometer illustrated in FIG. 2B.

Spatially multiplexed signal collection refers to the collection of light remitted from the sample into several fibers. FIG. 4 illustrated the interferometer 110 in FIG. 2B as interferometer 110' adapted to collect light from the sample 102 into two collection fibers 106, 106a to be detected separately, but heterodyned with the same reference field D2 provided via beamsplitter B3. This concept could be extended to many collection fibers.

Figure 5:
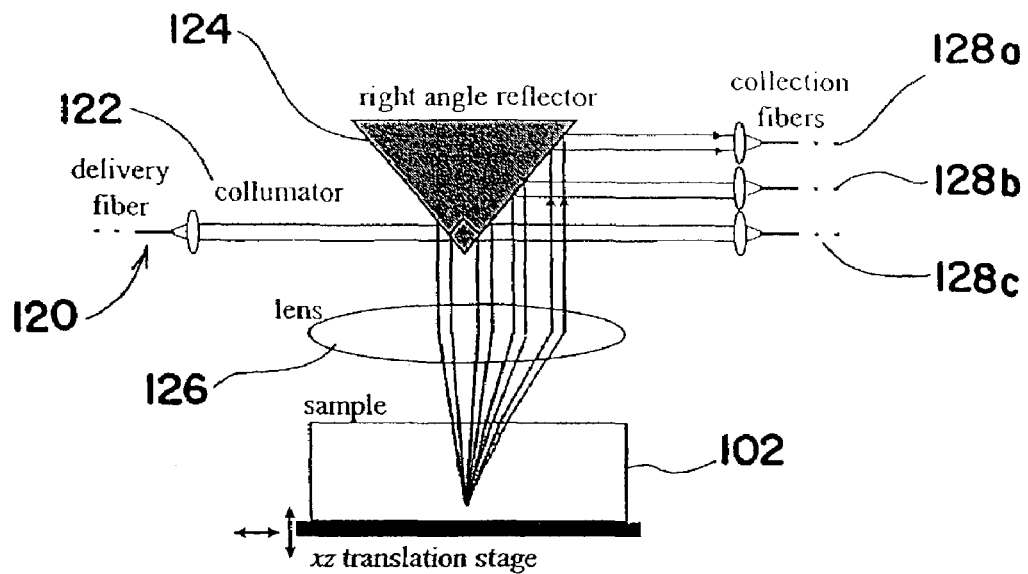
FIG. 5 is a schematic illustration of a spatially multiplexed interferometer in accordance with the present invention.

There are several possible applications for spatially multiplexed interferometer configurations. First, this may be a method to simultaneously measure signal light remitted from the sample at several scattering angles, perhaps as illustrated in FIG. 5. As illustrated, this method includes a delivery fiber 120, collimating lens 122, right angle reflector 124, lens 126, and collection lenses and fibers 128a–c. The sample 102 on a translation stage 130 can be moved in directions of the arrows. The purposes of this type of measurement will be discussed in section 3 below.

Figure 6:
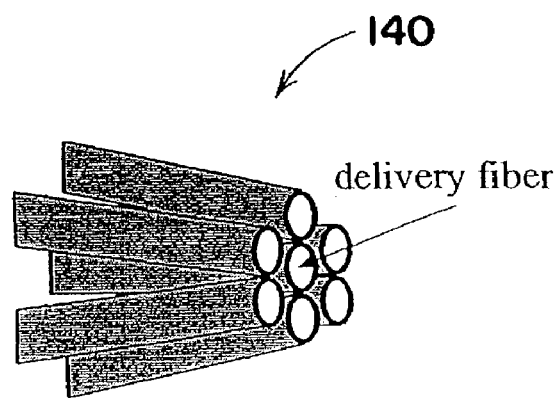
FIG. 6 is a schematic illustration of multiple collection fibers surrounding a single delivery fiber for use in conjunction with the interferometer illustrated in FIG. 5.

Extended to several collection fibers 140, as illustrated in FIG. 6 (illustrating an arrangement of multiple collection fibers, surrounding a single delivery fiber, for use with a spatially multiplexed OCT interferometer), this type of interferometer may prove useful as a method of improving image quality. If more probe light is collected from the sample 102 for use in imaging, then sensitivity will be increased. Hypothetically, if the sample light from each collection fiber 140 is interfered with a portion of the reference light, and detected in the shot noise limit, then the SNR for each will be the same as the SNR for a standard interferometer with a single detection fiber. These multiple signals could be combined in order to improve the overall SNR. Additionally, since each collection fiber will gather light from a slightly different angle, the speckle pattern detected by each will be different, so that when they are combined speckle will be suppressed.

Another possible use for an interferometer with multiple collection fibers is for use with color Doppler OCT. With CDOCT, absolute velocity measurement is only possible if the angle of the probe beam with respect to the direction of movement in the sample is known. If the angle is not known, then only relative velocity measurements can be made. Doppler shifted light is collected from two or more directions separated by known angles, however, then enough data is collected to calculate absolute velocity without a priori knowledge of the angle.

Figure 7:
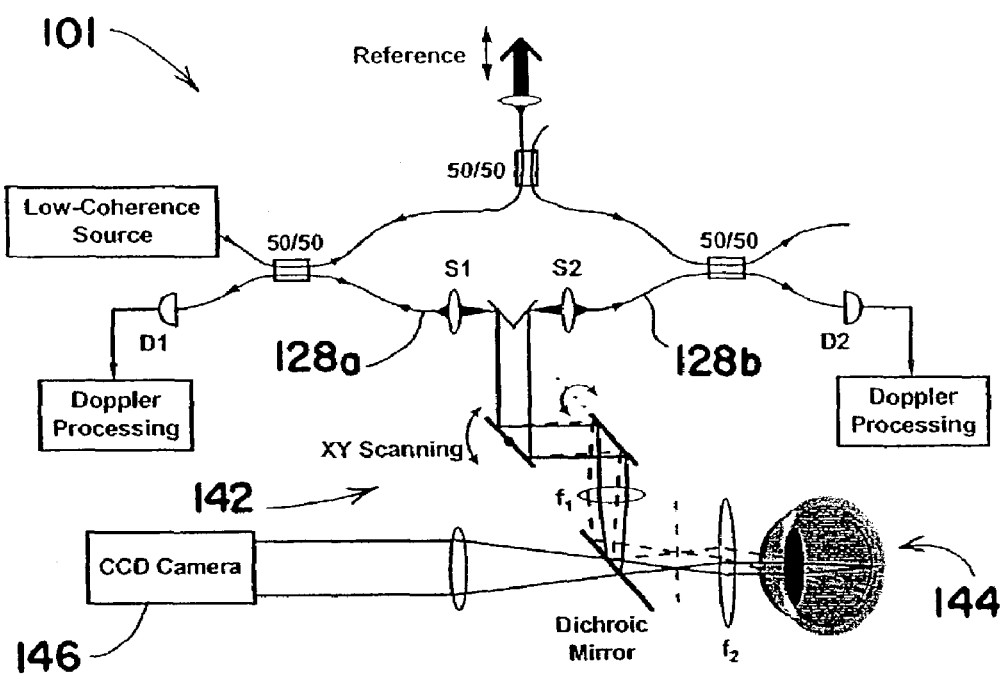
FIG. 7 is a schematic illustration of a dual beam CDOCT for absolute measurement of retinal flow.

Another application of spatially multiplexed signal collection is for absolute Doppler velocimetry using OCT. An example of an interferometer 141 and sample arm optics 142 appropriate for absolute Doppler OCT imaging in the retina 144 is shown in FIG. 7 (illustrating a schematic diagram of dual beam CDOCT for absolute measurement of retinal flow. Dashed lines indicate the beam path during scanning across the retina. $f_1$ and $f_2$ are the focal lengths for the telescope lenses). If light is collected in two distinct scattering directions (Riva 1979) separated by angle alpha α the difference in Doppler shifts arising from the two directions is related to the scatterer velocity by $$\Delta f = \frac{\alpha n_t v \cos\beta}{\lambda_0} = \frac{f_2}{f_e f_1} \frac{d n_t v \cos\beta}{\lambda_0}, \qquad (6.8.1)$$

assuming as the sample an eye with focal length $f_e$. In this expression, $v\cos\beta$ is the velocity component in the plane defined by the two scattering vectors, where Beta β can be approximated from direct viewing of the fundus using a CCD camera 146. Using an afocal telescope 148 in front of the eye, angular differences between two scattering directions (alpha α) translate to larger separations (d) between the two light beams re-coupling into the fibers. Since the separation between the two fibers remains fixed, a constant alpha α is always probed, thereby eliminating the Doppler uncertainty regardless of the beam position scanning along the retina, as indicated by the dashed lines in the figure.

Figure 8A:
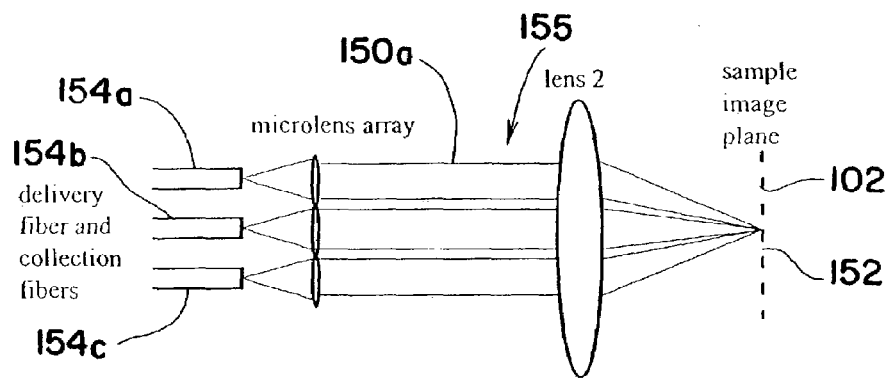
FIGS. 8A–8C are schematic illustrations of exemplary arm optics for simultaneously collecting light from a sample into multiple collection fibers.
Figure 8B:
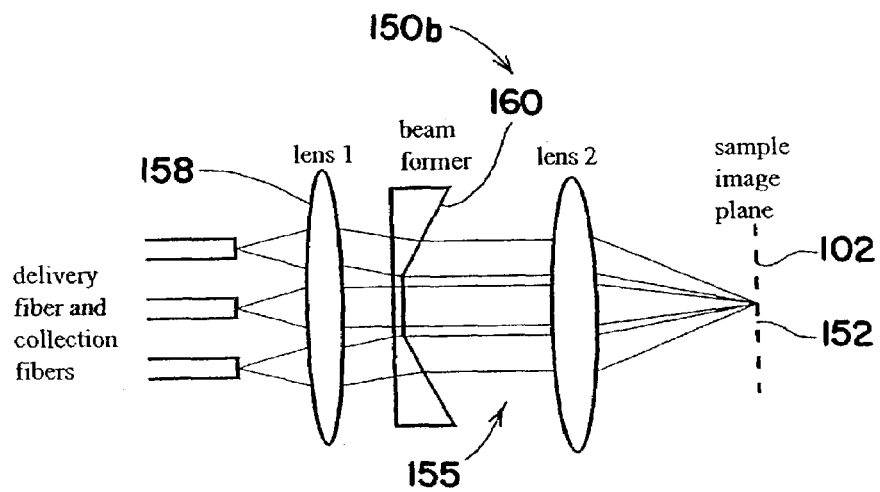
Figure 8C:
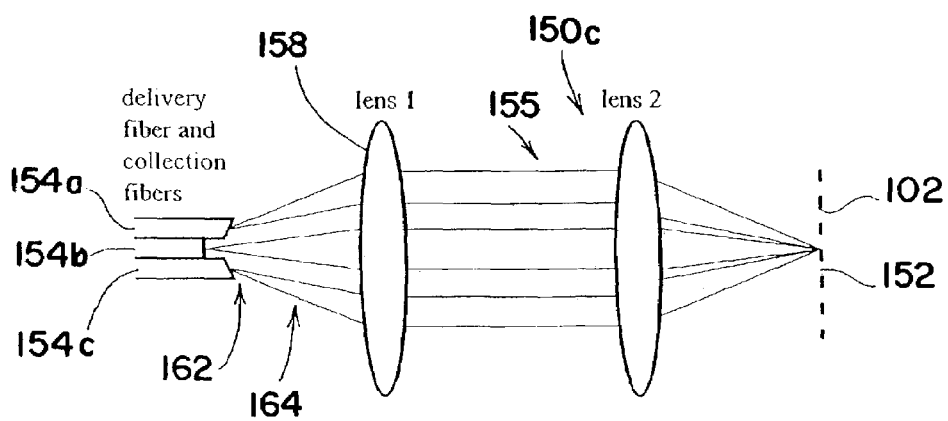

FIG. 8A–8C illustrate three examples of possible sample arm optics 150a–c for spatially multiplexed light collection. The object is to collect light from the same spot 152 in the sample 102 where the light is delivered. This is accomplished by designing an optical system that images the core of the delivery fiber 154a–c and each collection fiber to the same spot in the sample. In this way, a portion of the coherently backscattered wavefront 155 remitted from the sample is focused into each collection fiber 154a–c. In 8A, a micro-lens array 156 is placed in conjunction with the fiber array a54 to accomplish this. In 8B, a single lens (lens 1) 158 is used to collimate/focus light from/to each fiber and a beam former 160 (consisting in essence of a beam-deflecting prism for each collection beam) is used to correct the propagation direction of the remitted wavefront 155 such that it will be focused into the collection fibers 154a–c. It should be understood that the beam forming element 160 may be discrete prisms or a single integrated device, and that the prism angles must be designed exactly for prism material, light wavelength, and fiber spacing. In 8C, the fibers 154a–c themselves are oriented and angled 162 such that waves 164 emitted from each core approximately originate from the same virtual spot. In other words, the images of the cores overlap in the sample 102.

2.3 Acousto-Optic Modulator as Variable Beam Splitter

Figure 9:
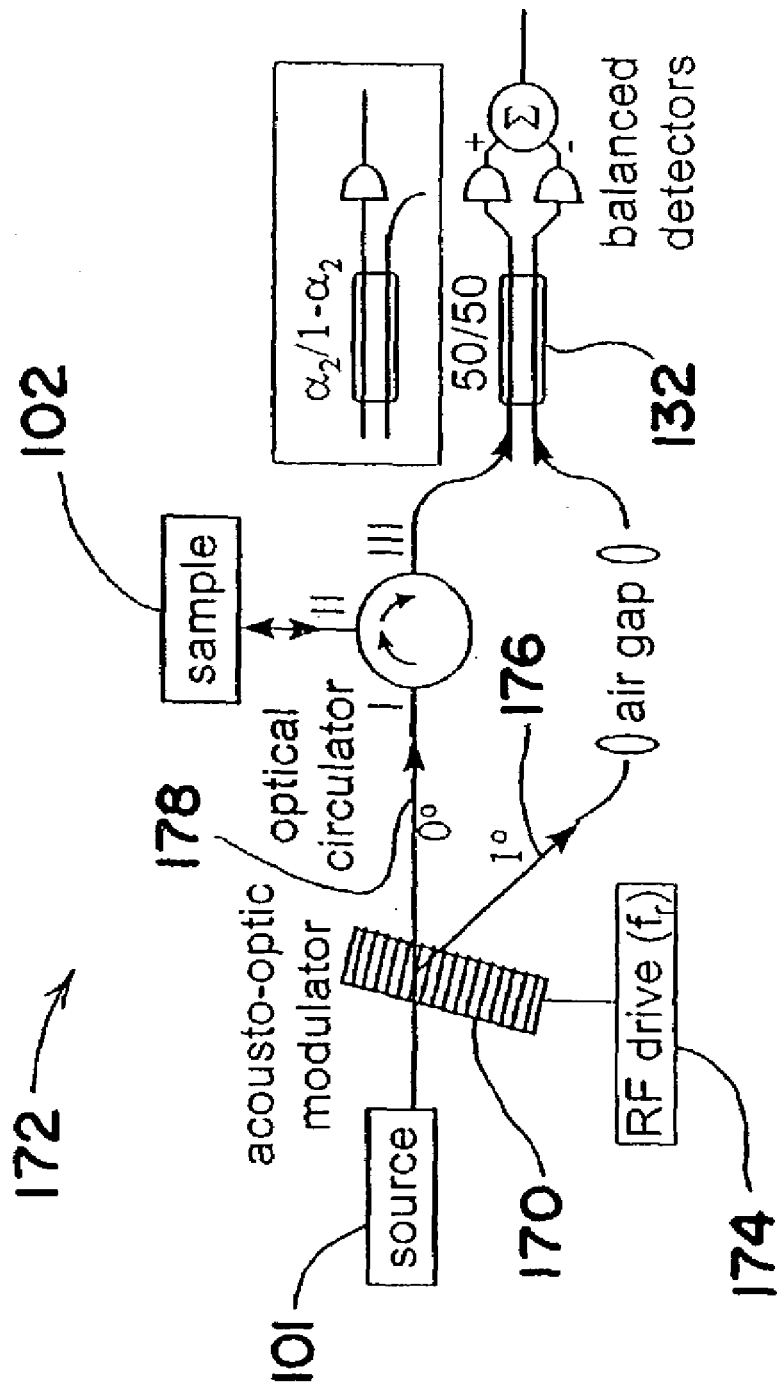
FIG. 9 is a schematic illustration of a Mach-Zehnder interferometer for OCT using an acousto-optic modulator (AOM) as a variable beam splitter.

The acousto-optic modulator (AOM) 170 in FIG. 9 may prove to be useful in OCT interferometers 172 as a variable beam splitter. Power-conserving interferometers are optimized by choosing the correct splitting ratio of the first splitter (and also the second, in the single detector cases). The optimal splitting ratio can be calculated if the optical source power and all of the losses in the system are measured and accounted for. In practice, this may not always be easy to do accurately, and a splitter with a variable splitting ratio could be an advantage. An AOM 170 is driven by a radio frequency (RF) signal 174. The frequency of the RF signal determines the angle into which the first order diffracted light 176 is coupled. The magnitude of the RF signal determines the diffraction efficiency, or the fraction of the incident light that is coupled into the first order. If the undiffracted (zero order) light 178 is directed to the sample 102, while the first order light is used as the reference D, then the AOM 170 acts as a variable beam splitter with the splitting ratio depending on the strength of the RF drive signal 174. Furthermore, AOMs are commercially available packaged with fiber pigtails for the input, and zero order and first order outputs. An illustration of an interferometer 172 for OCT using an AOM as a variable beam splitter is shown in FIG. 9.

Because the first order light is shifted by the RF signal frequency, heterodyne detection is possible without using a scanning optical delay line to Doppler shift the reference light D. Therefore, an AOM interferometer 172 could be especially useful for applications where a fast scanning delay line is not used. If the depth scan is slow, the Doppler shift imposed on the reference light D may not be sufficient to carry the signal sufficiently high above low frequency noise. In this case, the AOM 170 could provide the needed frequency shift. The relatively stable RF frequency shift may also be an advantage for velocity imaging using Doppler OCT imaging.

Another potential application of an AOM interferometer is for optical coherence microscopy (See J. A. Izatt, M. R. Hee, G. A. Owen, E. A. Swanson, and J. G. Fujimoto, "Optical Coherence Microscopy in Scattering Media," Opt. Lett., vol. 19, pp. 590–592, 1994, J. A. Izatt, M. D. Kulkarni, H.-W. Wang, K. Kobayashi, and M. V. Sivak, "Optical Coherence Tomography and Microscopy in Gastrointestinal Tissues," IEEE Journal of Selected Topics in Quantum Electronics, vol. 2, pp. 1017–1028, 1996, and H.-W. Wang, A. M. Rollins, and J. A. Izatt, "High-speed full-field optical coherence micrsocopy," presented at Coherence Domain Methods in Biomedical Science and Clinical Applications III, SPIE Photonics West, San Jose, Calif., 1999, which are incorporated by reference). Optical coherence microscopy (OCM) uses high NA optics to focus the probe beam into the sample, and scans laterally in two dimensions to form en face images. In this case the reference arm is stationary and an additional phase modulation or frequency shifting component must be used to take advantage of optical heterodyne. An AOM interferometer 172 can accomplish this without compromising efficiency like previous methods.

3 Angle Diversity for Pathlength-Resolved Elastic Scattering Spectroscopy

It is well established that measurement of light scattering from small particles can yield information about the size and distribution of the particles (See P. D. Kaplan, A. D. Dinsmore, A. G. Yodh, and D. J. Pine, "Diffuse transmission spectroscopy: A structural probe of opaque colloidal mixtures," Phys. Rev. E, vol. 50, pp. 4827–4835, 1994, J. R. Mourant, T. Fuselier, J. Boyer, T. M. Johnson, and I. J. Bigio, "Predictions and measurements of scattering and absorption over broad wavelength ranges in tissue phantoms," Applied Optics, vol. 36, pp. 949–957, 1997, and L. T. Perelman, V. Backman, M. Wallace, G. Zonois, R. Manoharn, A. Nusrat, S. Shields, M. Seiler, C. Lima, T. Hamano, I. Itzkan, J. Van Dam, J. M. Crawford, and M. S. Feld, "Observation of Periodic Fine Structure in Reflectance from Biological Tissue: A New Technique for Measuring Nuclear Size Distribution," Physical Review Letters, vol. 80, pp. 627–630, 1998, which are incorporated by reference.) In 1994, P. D. Kaplan et al. wrote of the technique of diffuse-transmission spectroscopy (DTS) (See P. D. Kaplan, A. D. Dinsmore, A. G. Yodh, and D. J. Pine, "Diffuse transmission spectroscopy: A structural probe of opaque colloidal mixtures," Phys. Rev. E, vol. 50, pp. 4827–4835, 1994, which is incorporated by reference.). This technique shown in FIG. 10 uses a broadband source 210 and monochrometer to produce a transmission spectrum that gives structural information about a colloid suspension. "Diffuse-transmission spectroscopy employs multiple scattering to probe the structure of optically opaque colloidal suspensions with weak photon absorption" [p. 4827]. DTS deduces structural information using a complex model, and was developed because most useful and interesting suspensions are optically opaque, i.e. they multiply scatter light. Single scattering systems, however can be probed for structural information much more directly. "Measurements of the scattered intensity as a function of scattering angle . . . provide explicit information about colloid structure. In fact, light scattering is useful in a wide variety of complex fluids which exhibit structures on length scales comparable to the wavelength of light, so long as multiple scattering can be neglected" [p. 4828]. Multiple scattering can be neglected in transmission or reflection measurements only if the sample is very weakly scattering, or if a gating system is employed to selectively detect only singly scattered light. Optical coherence tomography (OCT) is based on coherence gating and is a very effective gate for singly scattered light.

In 1997, J. R. Mourant, et al. published simulated and experimental light scattering data from tissue phantoms (See J. R. Mourant, T. Fuselier, J. Boyer, T. M. Johnson, and I. J. Bigio, "Predictions and measurements of scattering and absorption over broad wavelength ranges in tissue phantoms," Applied Optics, vol. 36, pp. 949–957, 1997, which is incorporated by reference.).

This study used the wavelength dependence of scattering to estimate particle size. Several conclusions they reached support the measurement of singly backscattered light for the probing of scatterers for structural information. "Measurements in geometries where high-angle scattering is enhanced are expected to be more useful for the differentiation of morphological features" [p. 954]. This is because scattering at high angles is more sensitive to structural differences such as particle size and distribution. Also, "measurements made with small source detector separations are more sensitive to the size of the scatterers than measurements made with large source detector separations. This is consistent with the results . . . that show that $\mu_s$ and $P(\theta)$ (probability distribution of scattering angles) are more sensitive to the size and shape of the scatterer than is $\mu_s'$ . . . In addition, scattering measurements with small fiber separations are expected to enhance sensitivity to high-angle scatter. This is because photons must turn around by way of high-angle scattering events to be detected" [pp. 954–955]. By these arguments, the ideal limit is the measurement of singly backscattered light. It should be noted that this discussion is of the measurement of scattering as a function of wavelength, as opposed to measurement as a function of angle. This measurement can also be made with OCT.

In January, 1998, L. T. Perelman, et al. published a very exciting letter in which the measurement of cell nuclear size distribution with diffuse reflectance spectroscopy is described (See L. T. Perelman, V. Backman, M. Wallace, G. Zonois, R. Manoharn, A. Nusrat, S. Shields, M. Seiler, C. Lima, T. Hamano, I. Itzkan, J. Van Dam, J. M. Crawford, and M. S. Feld, "Observation of Periodic Fine Structure in Reflectance from Biological Tissue: A New Technique for Measuring Nuclear Size Distribution," Physical Review Letters, vol. 80, pp. 627–630, 1998, which is incorporated by reference.).

This size distribution information was found to be encoded "in a fine structure component in backscattered light from mucosal tissue which is periodic in wavelength" [p. 627]. This fine structure is superimposed on and masked by the background diffuse reflectance spectrum. The signal is modeled as arising from light which is Mie backscattered by the epithelial nuclei, as well as light diffusely backscattered by the deeper tissue layers, and that portion of the diffusely backscattered light which is Mie forward scattered by the epithelial nuclei. The signal is measured and fit to a model of the diffuse reflectance based on photon diffusion theory. This fit is subtracted from the data leaving only the fine structure component. This component is related to nuclear size distribution using a formulation arising from Mie theory. Since forward scattered light is much less sensitive to particle size than backscattered light (See J. R. Mourant, T. Fuselier, J. Boyer, T. M. Johnson, and I. J. Bigio, "Predictions and measurements of scattering and absorption over broad wavelength ranges in tissue phantoms," Applied Optics, vol. 36, pp. 949–957, 1997, which are incorporated by reference.), the diffusely backscattered component of this measurement is essentially a lot of noise. OCT could effectively select only the singly backscattered light, thus making the measurement more accurate, and the calculations simpler. Also, OCT could add depth resolution to the measurements of nuclear size distribution. This could be a significant advantage in tissues such as colon mucosa, where the epithelium is not a flat surface, but forms deep crypts.

3.1 Potential Applications

As discussed above, one potential application of angle-resolved OCT (see FIG. 10) is the determination of particle size distributions in scattering media, such as colloidal solutions or biological tissue. The potential advantages of OCT over the methods referenced above include high spatial resolution (including resolution in depth), more effective rejection of multiply scattered light, and simpler calculations (due to the assumption of singly scattered light). Elastic single scattering spectroscopy using OCT has been proposed and demonstrated in preliminary experiments (See M. D. Kulkarni and J. A. Izatt, "Spectroscopic Optical Coherence Tomography," presented at Conference on Lasers and Electro-Optics, 1996, (See 1 M. D. Kulkarni and J. A. Izatt, "Spectroscopic Optical Coherence Tomography," presented at Conference on Lasers and Electro-Optics, 1996, which is incorporated by reference.). This idea is elegant and holds great potential. The major drawback is that light sources with very broad bandwidths that are appropriate for OCT are not readily available. This deficiency is the subject of intense research (See M. Bashkansky, M. D. Duncan, L. Goldberg, J. P. Koplow, and J. Reintjes, "Characteristics of a Yb-doped superfluorescent fiber source for use in optical coherence tomography," Optics Express, vol. 3, pp. 305–310, 1998 and W. Drexler, U. Morgner, C. Pitris, S. A. Boppart, F. X. Kartner, X. Li, S.-H. Cho, E. Ippen, M. E. Brezinski, and J. G. Fujimoto, "Subcellular optical coherence tomography with a kerr lens mode-locked Ti:A12O3 laser," presented at Coherence Domain Methods in Biomedical Science and Clinical Applications III, SPIE Photonics West, 1999, which are incorporated by reference.) and will surely not be a problem for long. Also, because OCT is a coherent measurement, wavelength dependent speckle effects will be present in addition to wavelength dependent Mie scattering. Angle-resolved OCT holds the potential to make an equivalent measurement without the need of a broadband source (though speckle may still be a problem). The drawback is the requirement of more complex instrumentation.

Another example of a potential application of angle-resolved OCT is the measurement of sarcomere lengths. Muscles are divided into fascicles, which are bundles of muscle fibers. Muscle fibers are composed of many myofibrils, which are composed of bundles of myofilaments organized into regular, periodic structures called sarcomeres, which are the basic functional units of muscle tissue. Because sarcomeres exhibit a periodic structure, they can act as a diffraction grating, diffracting light into a particular set of angles depending of the wavelength of the light and the pitch of the grating (i.e. the length of the sarcomere). Furthermore, as the sarcomere is the basic functional unit of the muscle, it contracts and expands with the muscle, changing it's length. Therefore, if light of a known wavelength is transmitted through muscle tissue, and the diffraction angles are measured, then the average length of the sarcomeres in that section of muscle can be calculated. This measurement is useful as a research tool, and as a method for monitoring muscle tension in reattachment surgeries. Currently, this technique is used by dissecting out a thin layer of a muscle, directing laser light through it, and detecting the diffraction angles in transmission. The technique is limited to transmission through thin slabs for the familiar reason that multiple scattering confounds the measurement. Again, because the OCT coherence gate is effective in selecting singly scattered light, angle-resolved OCT may be able to enable sarcomere length to be measured in reflectance mode on intact muscle, a great potential advantage.

3.2 Techniques

3.2.1 Scanning Angle

Figure 10:
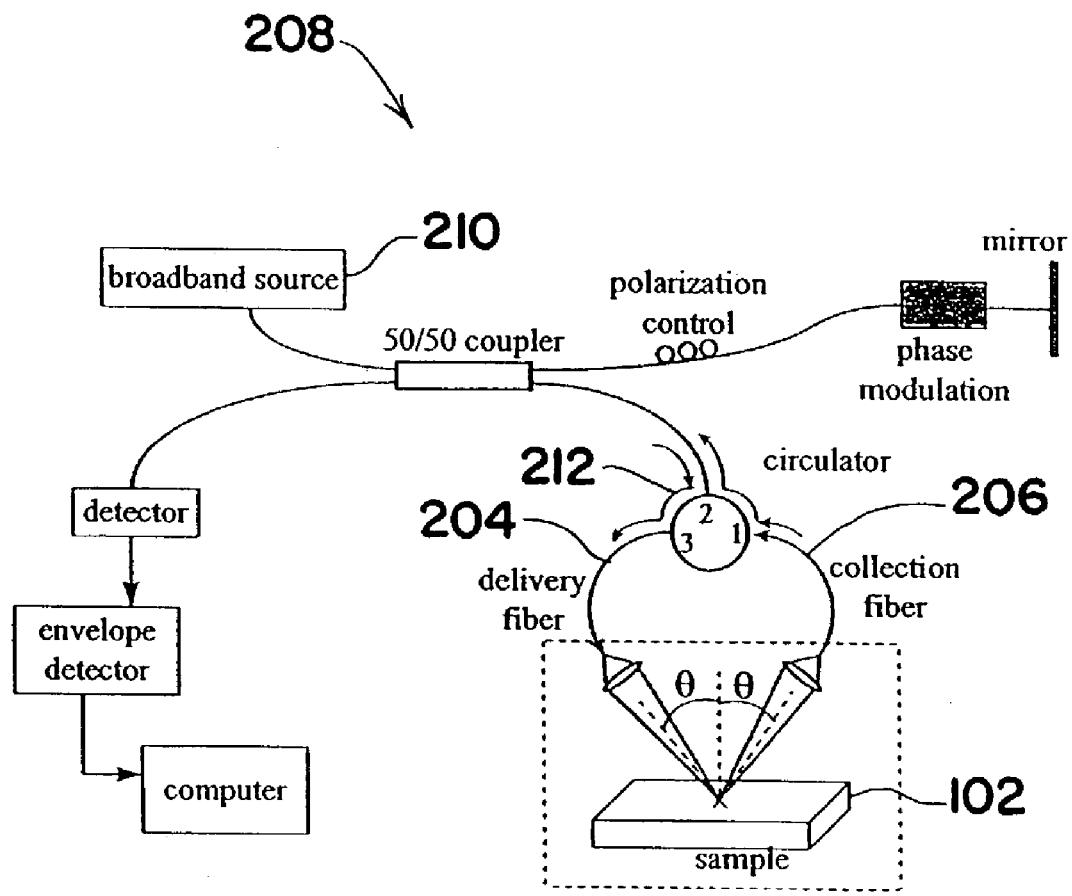
FIG. 10 is a schematic illustration of a Michelson OCT system to measure backscatter as a function of angle.
Figure 11:
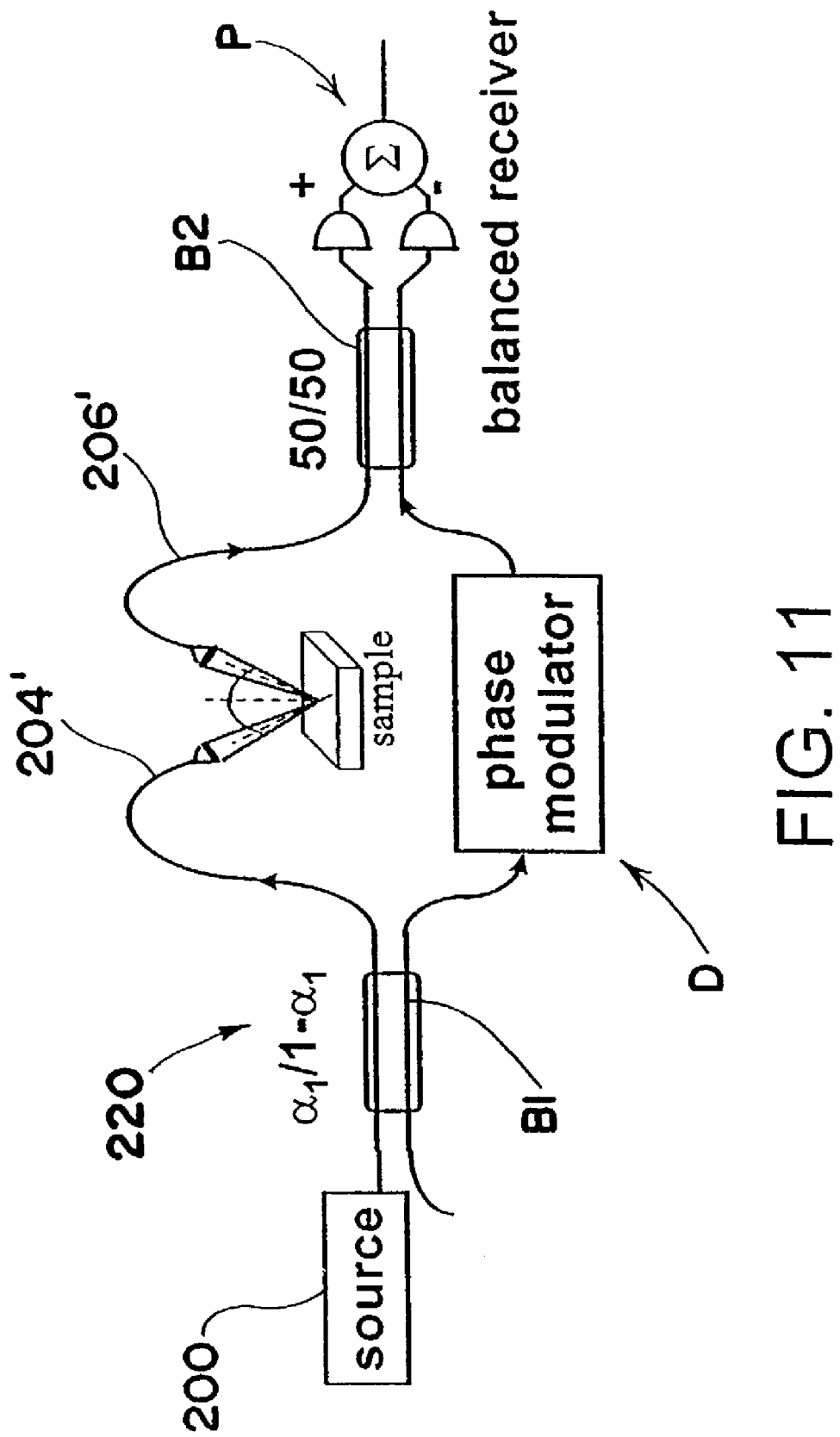
FIG. 11 is a schematic illustration of a Mach-Zehnder OCT system to measure backscatter as a function of angle.
Figure 12:
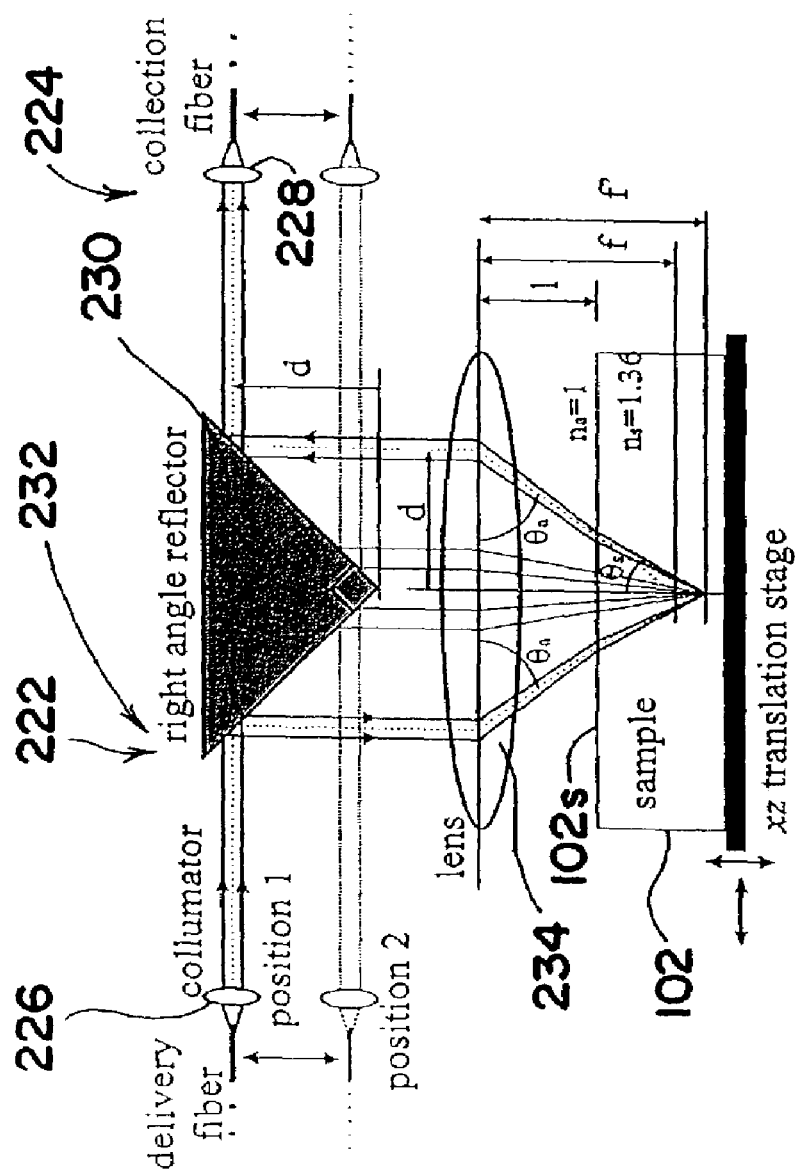
FIG. 12 is a schematic illustration of the apparatus to deliver and collect light in the sample arm of the device illustrated in FIG. 10.

In order to use OCT to measure scattering as a function of angle, I propose the setup described in FIGS. 10, 11 and 12. FIG. 10 illustrates a schematic of a Michelson OCT system to measure backscatter as a function of angle. As is described more fully below, the sample arm has an optical circulator used to allow light to be delivered and collected by different fibers. FIG. 11 illustrates a schematic of a Mach-Zehnder OCT system to measure backscatter as a function of angle. As is described more fully below, this design has several advantages over the Michelson design of FIG. 10, including increased efficiency and no need for a circulator.

OCT normally delivers light to the sample and collects it with the same fiber. This is a feature that selects almost exclusively singly backscattered light. To vary the scattering angle and thus collect light with a different scattering vector, it is necessary to use separate delivery and collection fibers, as shown in FIGS. 10 and 11. In order to operate as a leg in a fiber optic Michelson interferometer 208, though, the light must ultimately be coupled to and from the sample 102 in the same fiber leg of the 50/50 coupler. This is accomplished with an optical circulator 212. The circulator 212 couples all light from port 1 to port 2 and all light from port 2 to port 3, thus by connecting port 2 to the fiber beamsplitter, the light delivered to the circulator couples out of port 3 into the sample 102, and scattered light collected by port 1 is coupled back through port 2 to the interferometer 208.

An alternative design based on a Mach-Zehnder interferometer 220, is shown in FIG. 11. This design has several advantages over the Michelson design 208 of FIG. 10, including increased efficiency, and no need for a circulator 212.

As an angle is scanned, the optical path lengths of the delivery 204' and collection 206' sample arm optics must remain constant and matched. This can be achieved as shown in FIG. 12. The delivery and collection fibers 222, 224 are facing each other in line and the light is collimated 226, 228 such that with no obstruction, the light would be directly recoupled. A right angle reflector 230 is placed in the path of the beam such that the beam is deflected normally incident onto a large lens, which is a fixed distance from the reflector. Because the incident beam is off of the lens axis, the lens deflects the beam as it focuses the beam into the tissue sample 102. The beam makes an angle $\theta_a$ with respect to normal at the tissue surface 102s. This corresponds via Snell's law to an angle $\theta_s$ with respect to normal inside the tissue. This angle is a function of the lens focal length f, the tissue index of refraction n, and the distance d of the beam from the lens optical axis:

$$\theta_s = \arcsin\left(\frac{d}{n\sqrt{d^2 + f^2}}\right) \quad (6.9)$$

Because of symmetry, the collection fiber samples that portion of the light scattered at an angle of $-\theta_s$ with respect to normal. Thus the measured light is scattered at $2\theta_s$ from the backscatter direction. This angle can be scanned according to equation (6.9) by scanning the distance d. The distance d can be scanned by moving the pair of collimators 226, 228 vertically with respect to the reflector 230 and lens 234, as indicated by positions 1 and 2 in FIG. 12. The sample stage 236 can be translated to probe different locations in the tissue. For example, as calculated, with a 6 cm diameter lens with a focal length of 9 cm, scattering angles from approximately 420 to 28° (from the backscatter direction) can be measured.

3.2.2 Single-Shot With Angle Encoded in Frequency

Figure 13:
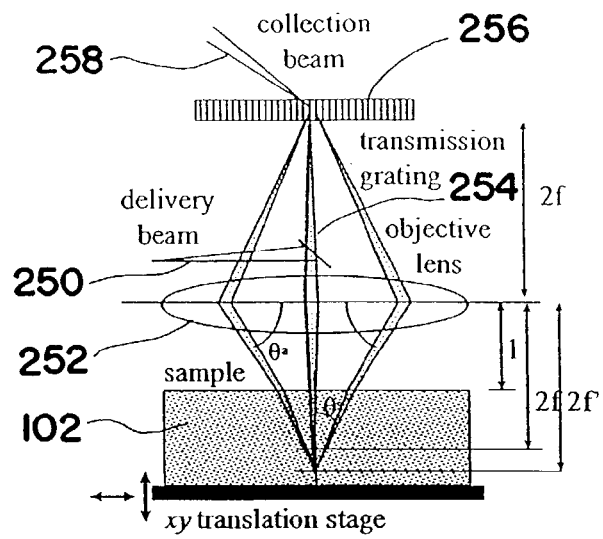
FIG. 13 is a schematic illustration of a method of measuring angle-resolved backscatter by spectrally encoding the scattering angle using a transmission grating.

FIG. 13 illustrates one method for use in the OCT systems of FIGS. 10–12, for example, of measuring angle-resolved backscatter without an angle scanning mechanism. The broadband probe light 250 is delivered to the sample 102 through a large diameter lens 252 (at 2f from the sample) by way of a small pick-off mirror 254. The probe light is scattered in all directions by the sample 102, but the large diameter lens 252 in combination with a transmission grating 256 (at 2f behind the lens) will collect a portion of the light 258 into a single spatial mode out of the grating, with each wavelength component having been scattered at a different angle, as shown in FIG. 13. The sample light 258 can be detected by an interferometer with a scanning reference arm D in the same manner as OCT, but the Fourier transform of the interferogram will represent the angular distribution of the scattering. This scheme measures a range of angles in a single shot, but the coherence gate is lost, and as the first order diffraction is used, sample light is lost into the zero order (undiffracted) and other orders. The advantage of optical heterodyne is retained, though, if an interferometer is used to detect the sample light. This scheme is similar to the technique of spectrally encoded confocal microscopy (SECM) proposed by Tearney, et al. (See G. J. Tearney, R. H. Webb, and B. E. Bouma, "Spectrally Encoded Confocal Microscopy," Opt. Lett., vol. 23, pp. 1152–1154, 1998, which is incorporated by reference.).

If the spectral information is not separated, the coherence gate is retained and $R_s$ at the common scattering point can be extracted. This is an inefficient OCT, but shows that the structure information can be collected simultaneous with the angle information and extracted simply by integrating over frequency.

Figure 14:
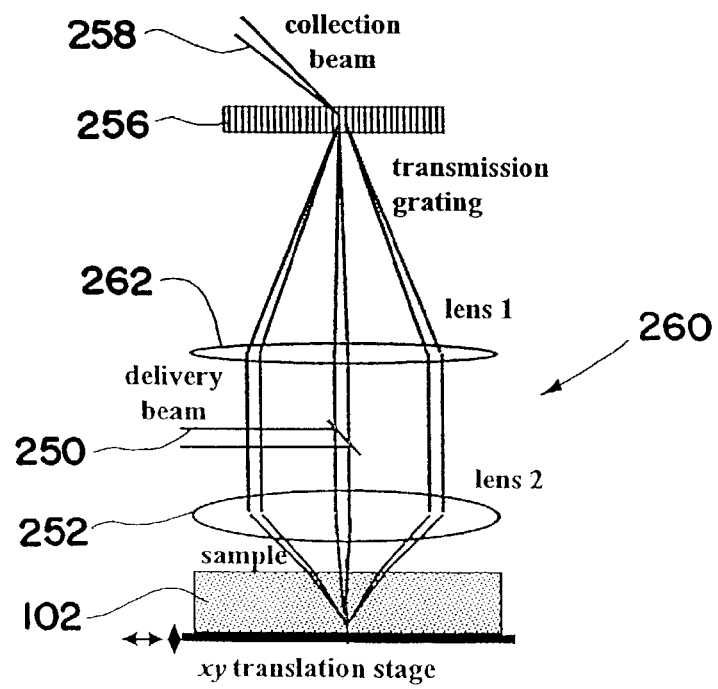
FIG. 14 is a schematic illustration of an alternative method of measuring angle-resolved backscatter by spectrally encoding the scattering angle using a transmission grating.

FIG. 14 illustrates another method of making the measurement illustrated in FIG. 13. Here a telescope 260 is used to image the scattered field from the sample on the transmission grating, which again selects into a single spatial mode wavelength components sampling light from different angles. The sample is one focal length from lens 2 (252) and the transmission grating is one focal length from lens 1 (262). Using a telescope 260 instead of a single lens allows the range of sampled angles to be magnified. In other words, a broader range of angles can be collected from the sample than the diffraction by the grating would allow in the configuration if FIG. 13.

Figure 15:
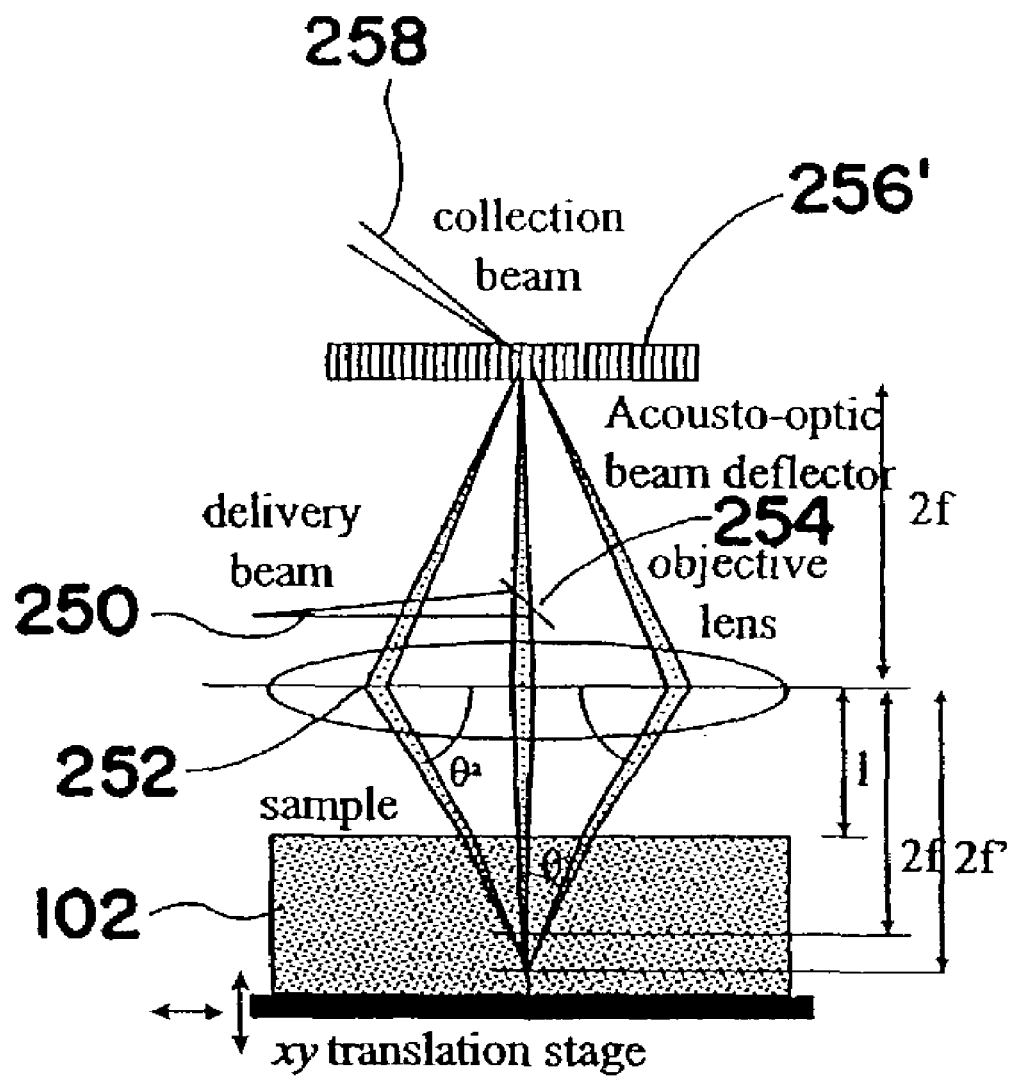
FIG. 15 is a schematic illustration of an alternative method of measuring angle-resolved backscatter by frequency encoding the scattering angle using an AOM.

FIG. 15 illustrates another method of measuring angle-resolved backscatter that is similar to the method illustrated in FIG. 13. In this case, an AOM 256' is used instead of a transmission grating. In this case, the scattering angle that is sampled depends on the frequency of the RF drive signal applied to the AOM 256'. The angles to be measured can be scanned by sweeping the RF drive frequency, or a multi-frequency RF signal can be applied to the AOM 256' in order to sample multiple angles simultaneously. The frequency shift imposed by the AOM allows heterodyne detection using an interferometer without a scanning delay line. If a low-coherence source is used, the coherence gate is retained with this scheme as well. Alternatively, a laser source can be used, but there will be no coherence gate of single-scattered light. Each scattering angle will be encoded with a unique RF frequency, so they can be separated by taking the Fourier transform of the optical heterodyne signal. It is to be appreciated that this single-shot method also increases the signal-to-noise ratio (SNR) and decreases speckle.

Figure 16:
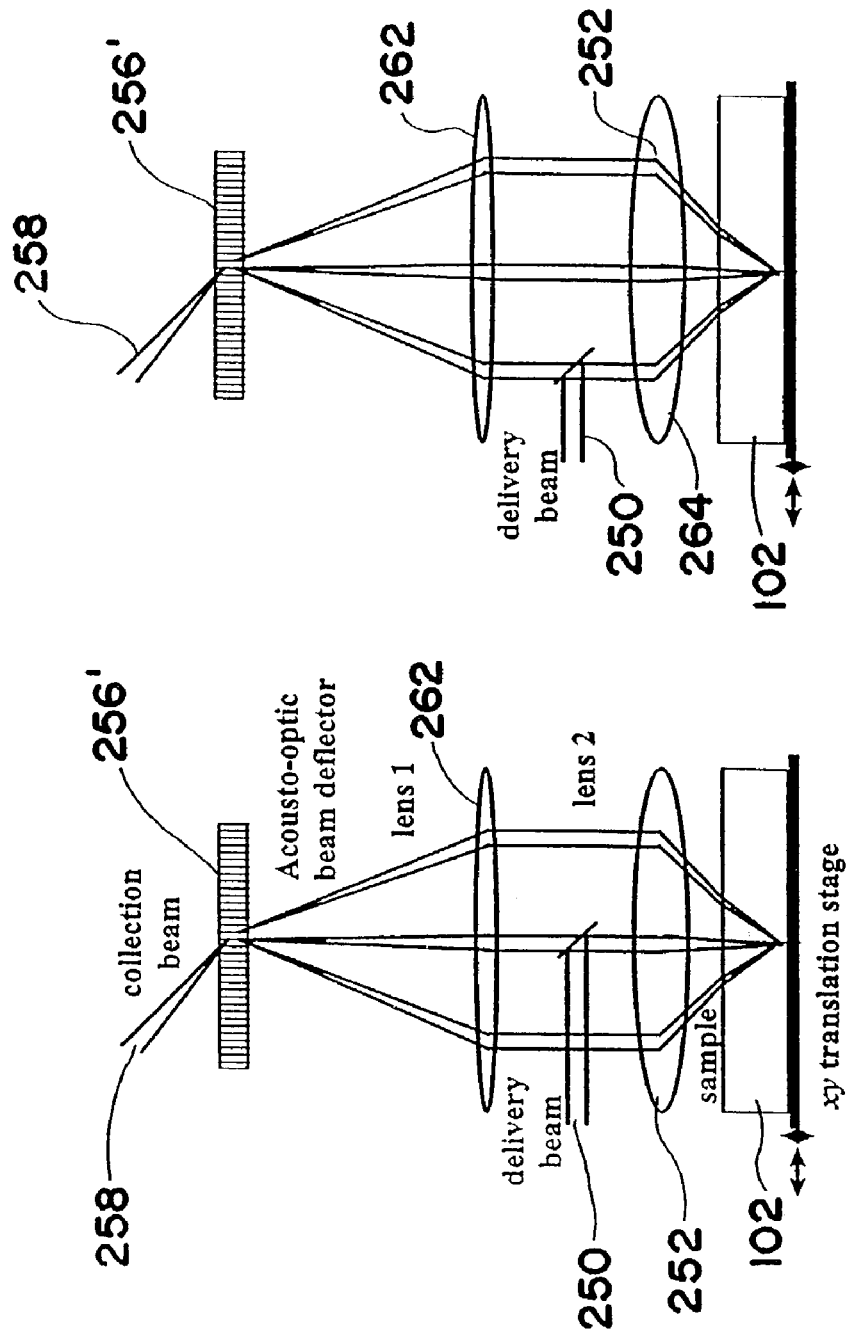
FIGS. 16A and 16B are schematic illustrations of alternative telescope embodiments of the AOM angle-resolved backscatter measurement illustrated in FIG. 15.

FIGS. 16A and 16B illustrate the telescope version of the AOM 256' angle-resolved backscatter measurement described in FIG. 15. This configuration is similar to the analogous configuration in FIG. 14. FIG. 16B also illustrates the fact that the delivery beam can be delivered to the sample from the side of the lens, rather than the middle, as has been illustrated in the figures above. The angle dependence of the backscatter intensity should be symmetrical about the direct backscatter direction, to delivering the beam through the center and detecting angles on either side is redundant. This redundancy can be used to reduce noise. Alternatively, if the beam is delivered at the side 264, as shown in FIG. 16B, then twice the angular deviation from direct backscatter can be measured.

4 Depth-Resolved Imaging of Action Potentials

Membrane potentials and action potentials in excitable cells can be measured optically using voltage sensitive (potentiometric) dyes (See R. P. Haugland, Handbook of Fluorescent Probes and Research Chemicals, 6 ed. Eugene, OR: Molecular Probes, which is incorporated by reference.). Usually this is done by perfusing the sample (heart or nerve tissue, for example) with the potentiometric dye and using a high speed camera to detect the surface potential distribution in real time. This technique has been a valuable research tool. One limitation of the technique is that it is two-dimensional. Only the surface of the sample is imaged and detecting the propagation of action potentials in three dimensions is a difficult problem. A technique of measuring the propagation of action potentials in three dimensions would be an important addition to this technique, particularly in the field of cardiac electrophysiology.

4.1 Background

4.1.1 Excitable Tissues

Electrical potentials exist across all cell membranes (membrane potential) and in many cases probably play a significant role in the management of cell activities (See A. C. Guyton, Textbook of Medical Physiology, 8 ed. Philadelphia, PA: W. B. Saunders Company, 1991, which is incorporated by reference.). Excitable tissues, such as muscle and nerve, are capable of generating potential impulses (action potentials) at their membranes, and in most cases, propagating these action potentials as a means of transmitting signals. Measurement of action potentials is an essential research tool in neuroscience and cardiology. One common method of measuring action potentials is by using intracellular microelectrodes. This is obviously invasive and is also restricted to measuring a single point for each electrode. As mentioned above, optical methods using potentiometric dyes are another useful method of measuring action potentials.

4.1.2 Voltage-sensitive Dyes

Potentiometric dyes enable the measurement of membrane potential with spatial and temporal resolution that is not possible using microelectrodes (See R. P. Haugland, Handbook of Fluorescent Probes and Research Chemicals, 6 ed. Eugene, Oreg.: Molecular Probes, which is incorporated by reference.). Furthermore, optical imaging can be used to map large areas simultaneously and also to measure structures and cells that are to small to be impaled by an electrode. Most potentiometric probes are used by illuminating the sample with an excitation light, and measuring the voltage-dependent fluorescence. Some dyes exhibit a voltage dependent absorption spectrum and absorption is measured to transduce potential. Potentiometric dyes can be classified as slow probes and fast probes. Slow probes change their optical properties as a result of voltage-dependent distribution in the membrane. These are useful for measuring the membrane potential of non-excitable cells. Fast probes change their optical properties as a result of a voltage-dependent change in their electronic structure, and therefore their excitation and emission properties. These probes have a typical response time on the order of milliseconds and are useful for measuring action potentials.

4.2 Techniques

4.2.1 Direct Absorption Contrast

The most straightforward method of using OCT to measure a voltage dependant dye is to choose and absorption probe and simply image the sample. Increased absorption by the dye would decrease the signal remitted by the sample. It may be possible to use the dispersion spectroscopic OCT described in section 6.1.2 to measure the absorption directly, avoiding the influence of scattering and speckle. This may be particularly useful if the absorption peak is sharp with respect to the bandwidth of the OCT light source.

4.2.2 Differential Absorption Contrast (see 1.1)

Another way to avoid the effect of scattering on the measurement of the absorption spectrum may be to measure the differential absorption between two distinct wavelengths using wavelength ratiometric OCT as described in section 6.1.1. This may be particularly useful if the absorption bandwidth is similar to or broader than the bandwidth of the optical source.

4.2.3 Stimulated Emission

It may be possible to use OCT to detect a fluorescent potentiometric probe through the generation of stimulated emission. If the sample is pumped by strong light source at the excitation wavelength of the probe, and the sample is imaged by an OCT system using a light source that corresponds to the emission band of the florescent probe, then the OCT signal may be enhanced by stimulated emission of fluorescence. This stimulated fluorescence emission should be a function of membrane potential. With this technique, the pump light could be chopped in order to provide a reference frequency for the detection electronics to lock in to, increasing sensitivity to membrane potential. Again, if the direct intensity measurement is not sensitive enough in the presence of scattering and speckle, then the spectroscopic techniques described above could also prove useful with stimulated emission.

This technique, of course, could also potentially be used to measure stimulated emission from other sorts of fluorescent probes, opening OCT to an unlimited number of applications in biomedical sciences. Perhaps even tissue autofluorescence could be measured with depth resolution in unprepared samples.

5 Dual Source Optimum Interferometer for OCT

Figure 17:
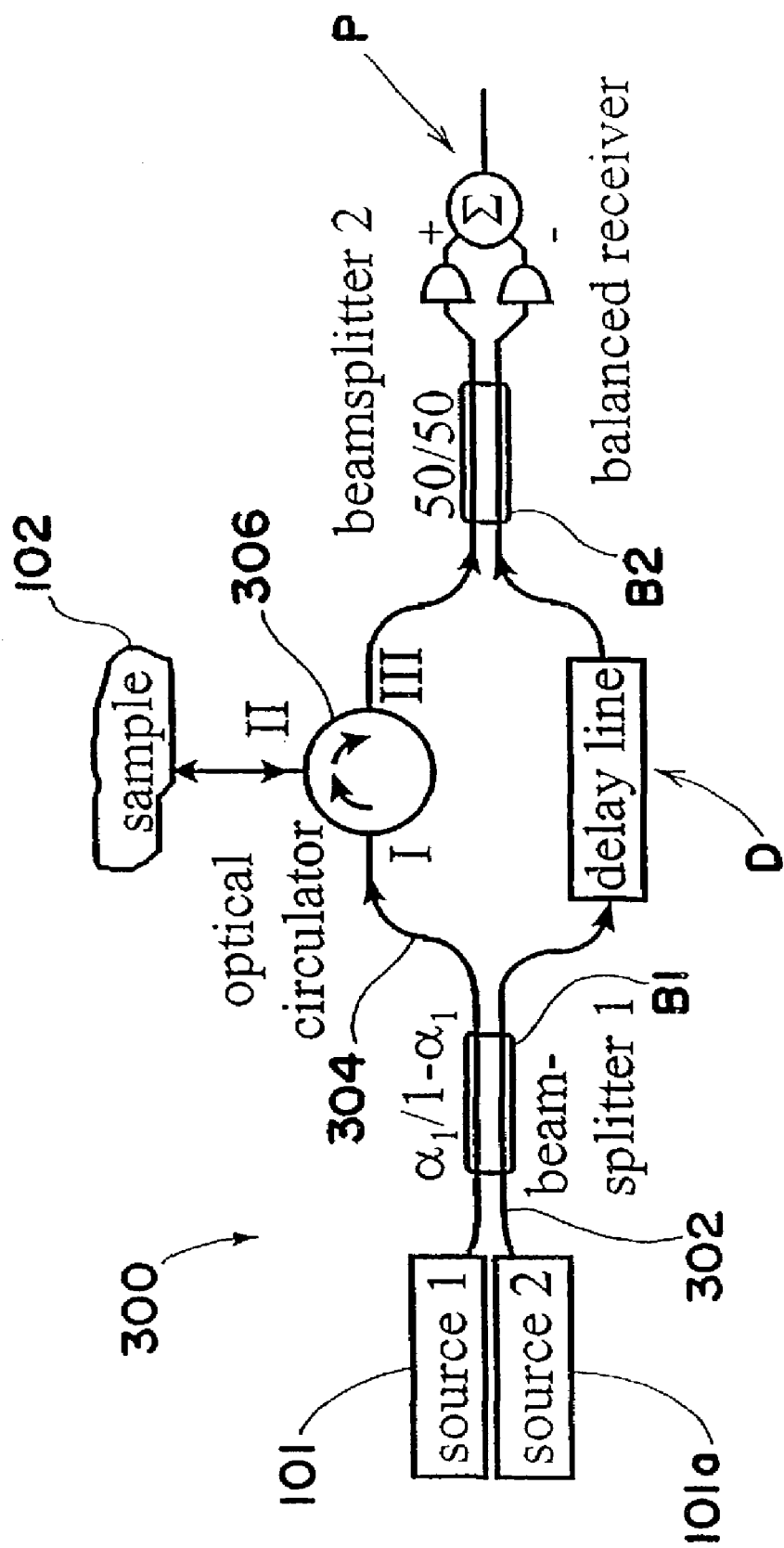
FIG. 17 is a schematic illustration of a dual source fiber optic OCT interferometer in accordance with the present invention.

An optimal fiber-optic OCT interferometer design 300 which incorporates a feature that has not been previously disclosed is illustrated in FIG. 17. The interferometer 300 layout in this Figure is very similar to one we published (See A. M. Rollins and J. A. Izatt, "Optimal interferometer designs for optical coherence tomography," Optics Letters, vol. 24, pp. 1484–1486, 1999, which is incorporated by reference.), with the exception that we here suggest the possibility to add a second optical source 101a to the second input 302 of the first beamsplitter B1. This second source 101a admits the possibility of increasing the power and extending the bandwidth of the illumination light (by choosing a second light source with a spectrum displaced from that of the first 101), or else of increasing the power alone by choosing a second source 101*a* with a similar spectrum to the first. Whether this option is exercised or not, light from one or both sources 101, 101*a* is split into sample 304 and reference D arms by the (potentially) unbalanced fiber beamsplitter 1 (B1). The splitting ratio of this beamsplitter may be chosen in accordance with the SNR analysis published by Rollins et al (See A. M. Rollins and J. A. Izatt, "Optimal interferometer designs for optical coherence tomography," Optics Letters, vol. 24, pp. 1484–1486, 1999, which is incorporated by reference.). Light in the sample 304 and reference arms D is directed to the sample 102 and to a rapid scan optical delay (RSOD), respectively. The sample light can be directed to the sample by an optical circulator 306, as shown in FIG. 17, or alternatively, transmissive sample optics may be used as described previously in this disclosure. The reference light can be directed to the optical delay line D by an optical circulator (not shown), or alternatively, a transmissive delay line may be used as shown in FIG. 17. One example of an RSOD which could be used for this purpose is a Fourier-domain optical delay line described (See A. M. Rollins, M. D. Kulkarni, S. Yazdanfar, R. Un-arunyawee, and J. A. Izatt, "In Vivo Video Rate Optical Coherence Tomography," Optics Express, vol. 3, pp. 219–229, 1998 and G. J. Tearney, B. E. Bouma, and J. G. Fujimoto, "High Speed Phase- and Group-Delay Scanning with a Grating-Based Phase Control Delay Line," Optics Letters, vol. 22, pp. 1811–1813, 1997, which are incorporated by reference.). Light returning from the sample 102 and reference arms D is combined in the balanced fiber beamsplitter 2 (B2), and then directed into a differential detector pair P. The signals from the detector pair P are subtracted, and then processed and displayed according to methods previously described.

Technologies for High Speed Optical Coherence Tomography (OCT)

1. Hardware Double-sided Scan Correction

Figure 18:
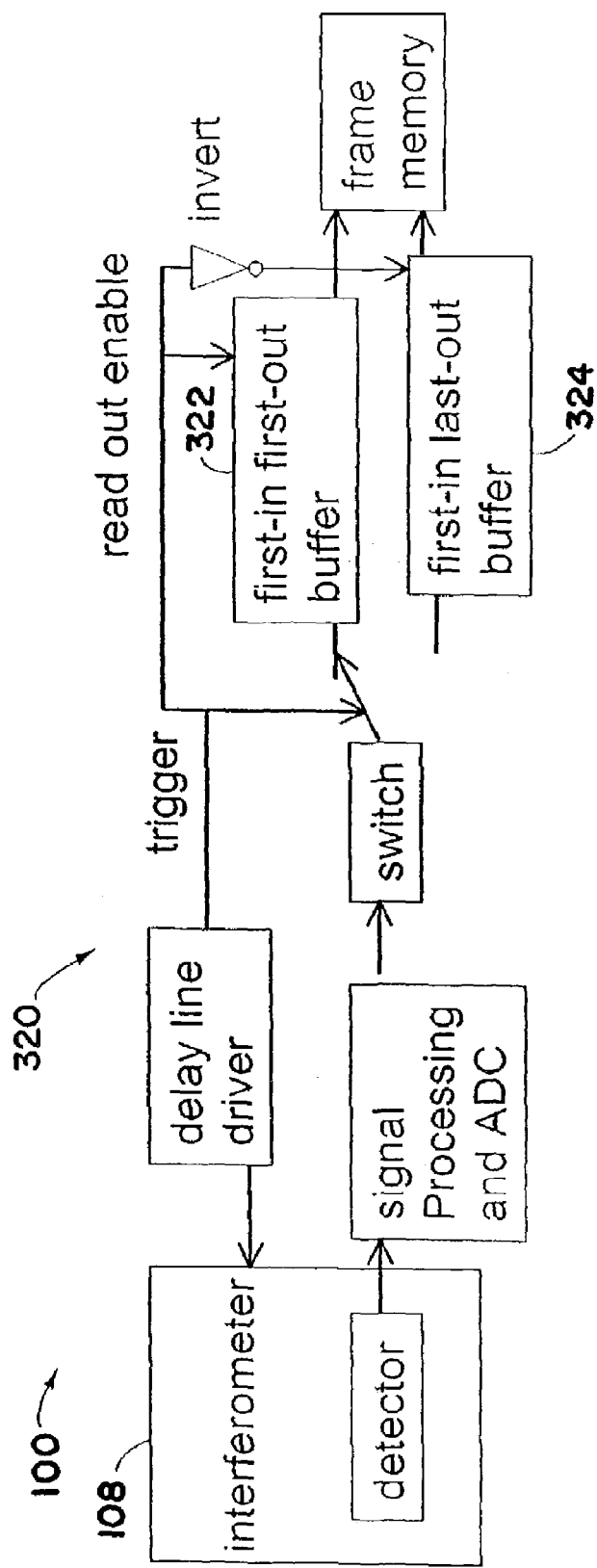
FIG. 18 is a schematic illustration of an OCT system utilizing double-sided scanning in accordance with the present invention.
Figure 19:
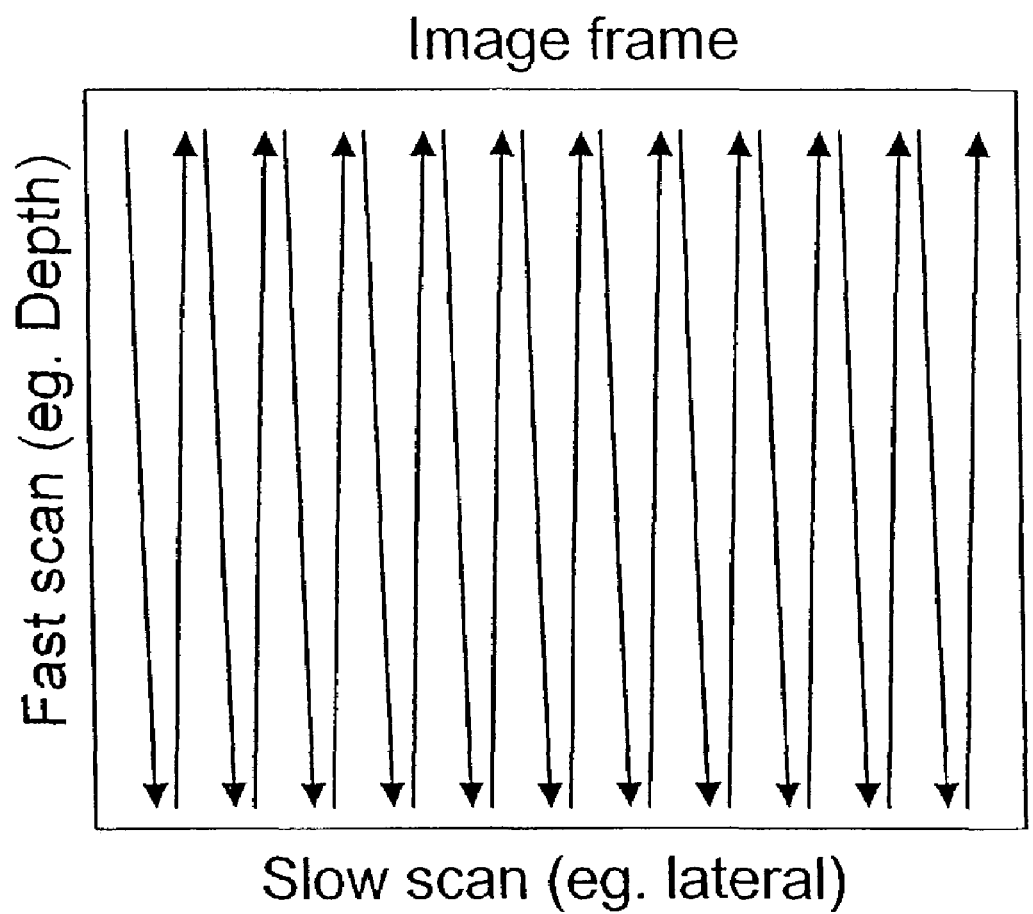
FIG. 19 is an exemplary A-scan acquisition utilizing the system illustrated in FIG. 18.

When an OCT system (e.g., as shown at 320 in FIG. 18) utilizes double-sided scanning (e.g., A-scan acquisition during both directions of the reference arm scan, e.g., as is represented in FIG. 19), a transformation is necessary to rectify the alternate, reversed A-scans. Data resulting from double-sided scanning can be corrected in hardware using two buffers 322, 324, one for the forward scan and one for the reverse scan, e.g., as is represented in FIG. 18. The forward scan buffer 322 is first-in-first-out while the reverse scan buffer 324 is first-in-last-out. The data is multiplexed into the two buffers alternately, and read out alternately.

2. Efficient Rapid Scanning Optical Delay Line

Figure 20:
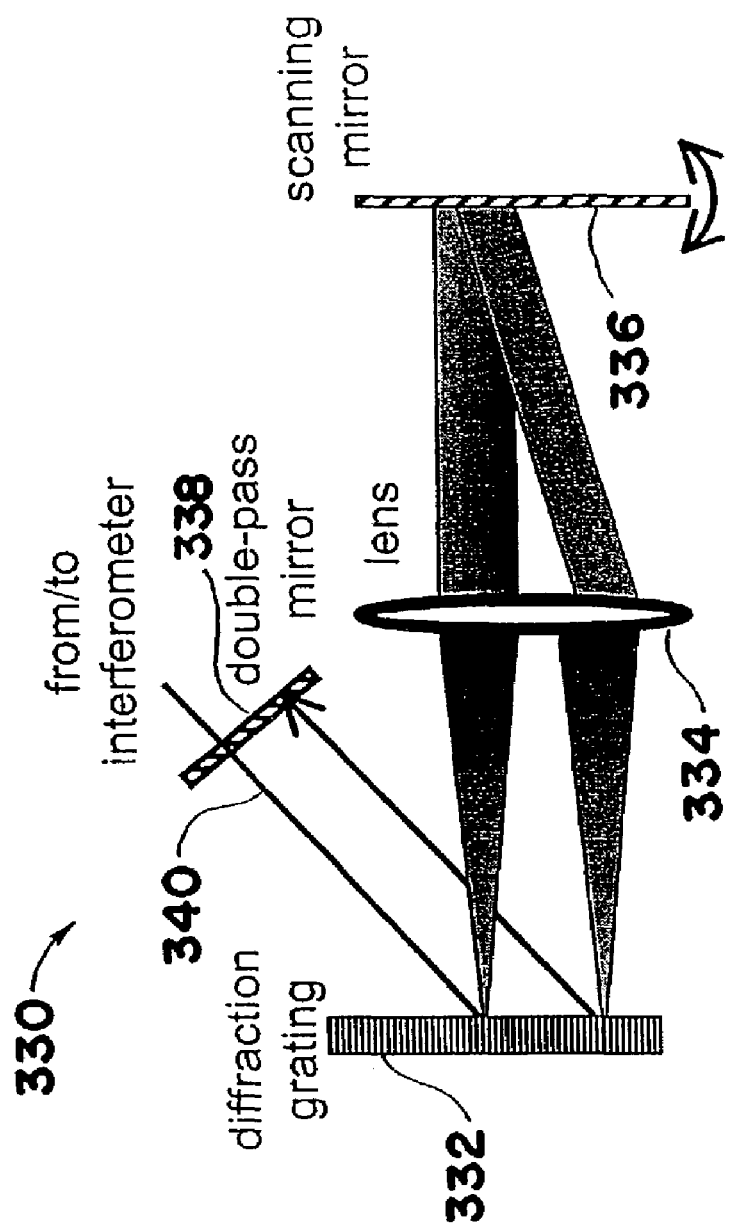
FIG. 20 is a schematic illustration of a rapid scanning optical delay (RSOD) line for use in conjunction with the OCT system illustrated in FIG. 18.

The rapid scanning optical delay (RSOD) line 330 (FIG. 20) of an interferometer, such as that shown at 320 in FIG. 18, consists of a diffraction grating 332, a lens 334, a scanning mirror 336, and a double-pass mirror 338. This delay line 330 has successfully enabled high speed optical coherence tomography [Kwong, 1993 #16; Tearney, 1997 #26; Rollins, 1998 #444]. One disadvantage of this delay line, however, is that it is very lossy due to multiple diffractions off of the grating 332. In a double-pass configuration, the beam 340 is diffracted four times into the first order. Even if the grating 332 is as efficient as 50% diffraction into the first order, 12 dB, or almost 95% of the light incident on the delay line is lost. This loss could be reduced by replacing the diffraction grating 332 with a more efficient dispersive element, for example, a transmissive dispersive element, such as a prism 342 (FIG. 21).

3. Switchable Depth Settings

In a clinical OCT system, it is often necessary to have more than one image size available. For example, referring to FIGS. 22 and 23 in an anterior segment ophthalmic OCT system, two depth settings may be desirable, one of approximately 2.5 mm depth for imaging the cornea, and one of approximately 6 mm depth for imaging the entire depth of the anterior chamber. This range can be accommodated by providing a deep scan and via software only displaying the desired portion of the scan. This technique has the disadvantage of inefficiency because the longer the scan at a fixed repetition rate, the broader the bandwidth of the signal and therefore the worse the SNR (signal to noise ratio). The scan depth can be continuously varied with the RSOD and other common OCT delay lines simply by varying the amplitude of the signal driving the scanner. A continuous range of scan depths has the disadvantage of inconvenience in a clinical setting. Two or more pre-determined scan depths can be provided by implementing a switchable amplitude adjustment 350 (FIG. 23) for the signal driving the scanner. Changing the scan velocity changes the center frequency and bandwidth of the OCT signal. In order to accommodate the changing signal, switchable demodulation electronics can be provided which optimally match each depth setting. An example of a sub-system to do these functions is the switchable amplitude adjustment 350 of FIG. 23, which includes switch 352 that operates the delay line scan length control 354, the demodulation settings, e.g., filters, etc., 356, and the lateral scan length control 358. If desired, scanning at specified depths, e.g., two different depths, may provide two different size images 360, 362 shown in FIG. 22. The smaller image, e.g., 5 mm to 3 mm, may be for imaging the corner and angle; and the larger image, e.g., 16 mm by 7 mm to image the entire anterior segment of an eye.

4 Compensation for Nonlinear Scanning

If the scan rate of the OCT optical delay line fluctuates or varies, then the carrier frequency and bandwidth of the OCT signal vary proportionately. If the bandwidth of the demodulation electronics is broadened to accommodate this variability, then SNR is compromised. Also, an acquired OCT image will be warped if the spatial distribution of the acquired data does not directly correspond to the spatial distribution of scattering profile of the sample. This occurs in OCT imaging when the image data is not sampled at regular intervals in space. For example, if the scanning motion of the OCT probe or delay line is not linear with time, and the data is sampled at regular intervals in time, then the image will be warped. Several techniques can compensate for or correct these consequences of non-linear scanning.

Figure 24:
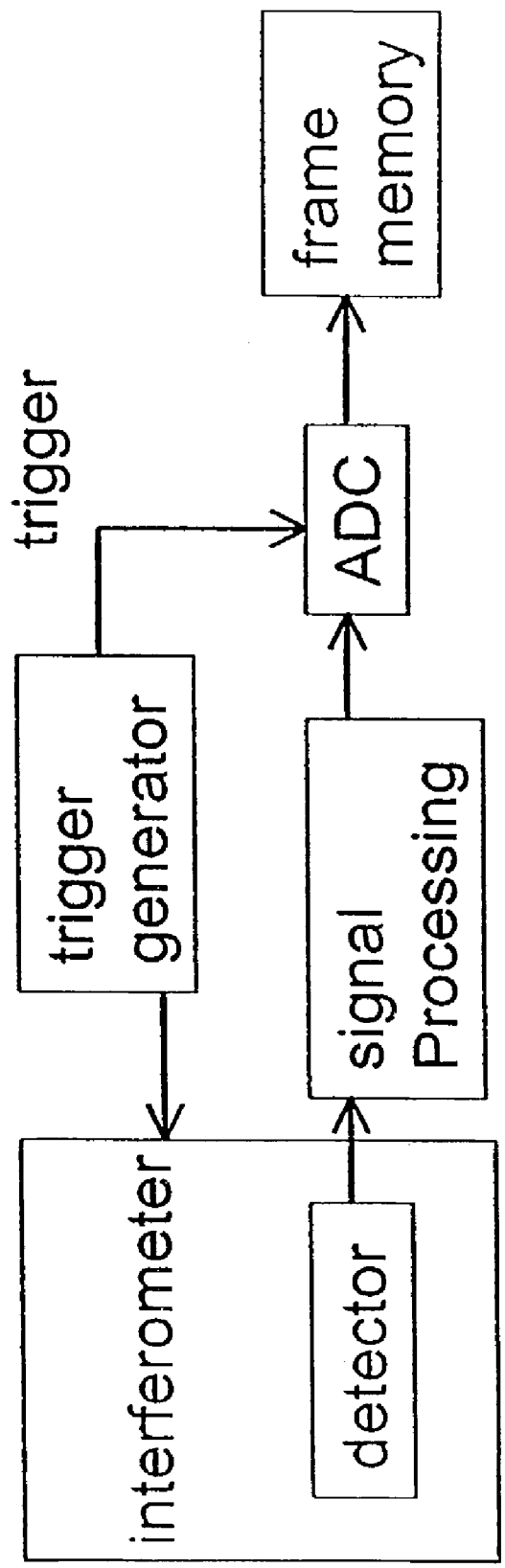
FIG. 24 is a schematic illustration of device for generating a sampling trigger signal in accordance with the present invention.

If the scan nonlinearity is a known function of time, however, the image can be 'de-warped' by an appropriate spatial transformation. This is the case, for example, for the sinusoidal motion of a resonant scanning device. In this case, the coordinate corresponding to the resonant scanner can be transformed by a sinusoidal function with a period corresponding to the period of the scan in image space. Alternatively, if an accurate reference signal is available, for example, from the delay line driver, or from a reference interferometer, a corresponding sampling trigger signal could be generated to sample nonlinearly in time such that the image is sampled linearly in space (FIG. 24). This latter technique is common in Fourier transform spectrometers, and has previously been applied in high-accuracy interferogram acquisition in OCT [Kulkarni, 1997 #396].

Figure 25:
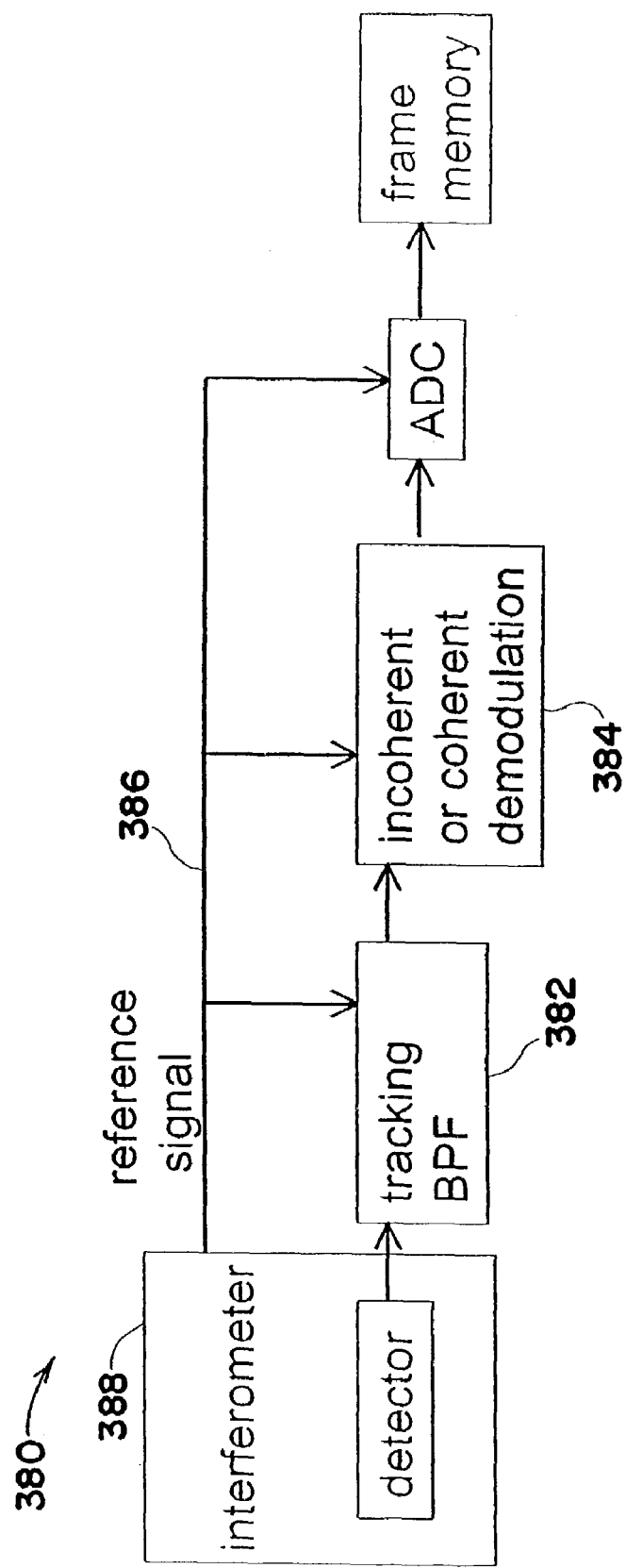
FIG. 25 is a schematic illustration of a method of preserving SNR in an OCT system having a nonlinear scan rate.

One method of preserving SNR in the case of a nonlinear scan rate of an OCT system 380, e.g., as shown in FIG. 25, as results for example from the use of a resonant scanning device, is to implement a tracking bandpass filter 382. The tracking bandpass filter 382 would track the center frequency of the OCT signal and would be followed by an incoherent demodulator 384 (rectifier, or envelope detector) or could be followed by a tracking coherent demodulator. One method of implementing a tracking bandpass filter 382 is to use a signal corresponding to the scanner waveform (for example, the drive waveform, or the output of an analog position encoder) to drive a voltage controlled oscillator (VCO). The oscillator acts as a bandpass filter. The signal driving the VCO must be exactly in phase with the motion of the scanner. At the same time, the output of the VCO, or the reference signal 386 from the interferometer 388 could be used to generate a sampling trigger (pixel clock) in order to provide a nonlinear sampling rate that matches the nonlinear scan rate. In that way, the signal will be sampled regularly in space and the image will not be distorted or warped. If the VCO frequency is higher than the desired sampling rate, then the VCO output can simply be digitally divided down to the desired sampling rate.

Figure 26:
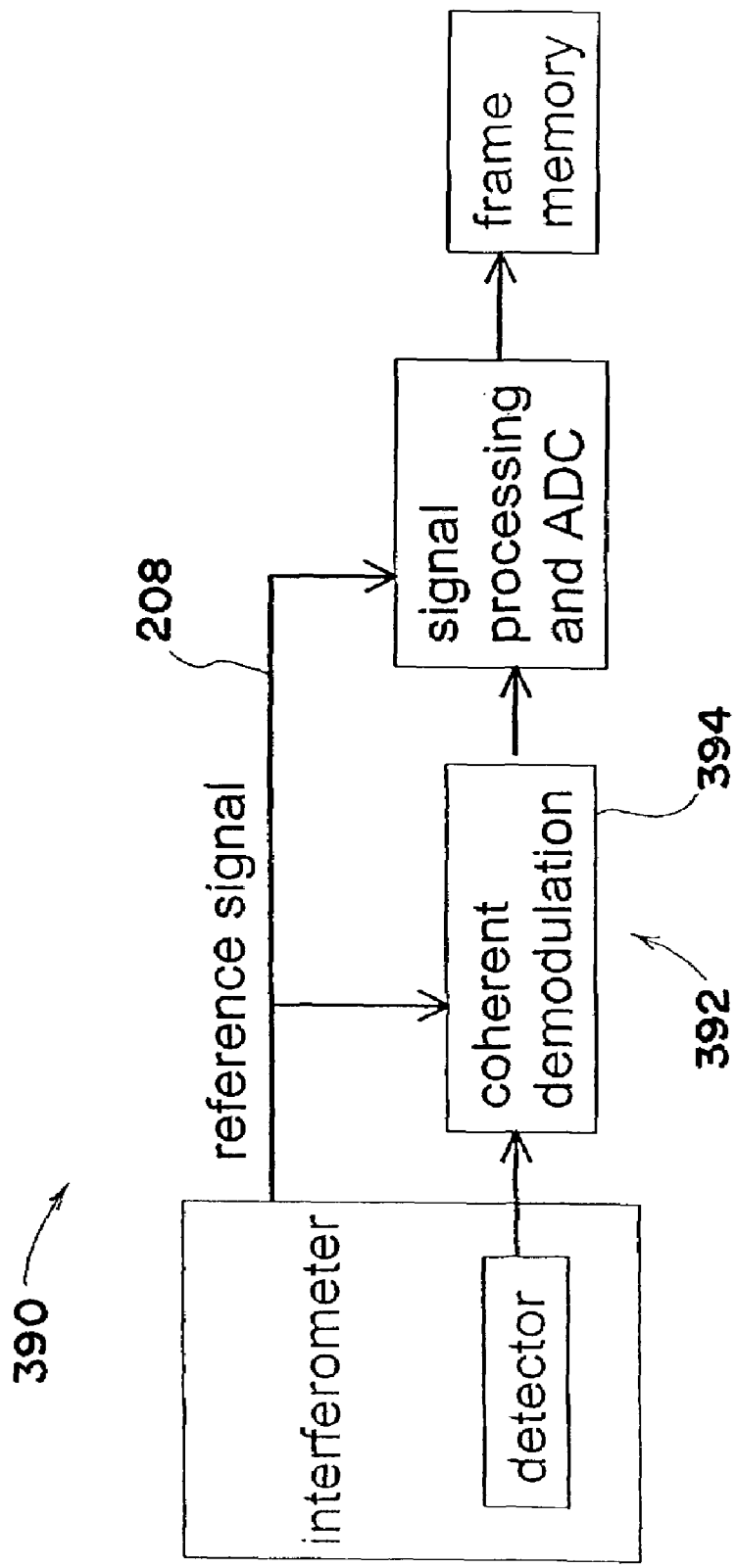
FIG. 26 is a schematic illustration of an alternative method of preserving SNR in an OCT system having a nonlinear scan rate.

Another method of preserving the SNR in the case on a nonlinear scan rate is to implement a scanning demodulator as shown in an OCT system 390 at 392 in (FIG. 26). In this technique a local oscillator (LO) signal is generated with a frequency that varies exactly as the center frequency of the OCT signal varies. The LO is used to demodulate 394 the time-varying OCT signal to a fixed intermediate frequency (IF) or to DC. This mixing step would be followed by a static bandpass or lowpass filter and envelope detection or baseband demodulation 394 if necessary. The LO signal could be used to generate a pixel clock associated with the ADC (analog to digital converter) in the way described above in order to prevent image warping. The tracking LO signal can be generated in any suitable manner. For example, the scanner drive signal or analog position indicator signal can be used to drive a VCO to provide the tracking LO. Or, the lowest bit of a digital scanner position encoder can be used directly or divided down to provide the tracking LO. Or, a reference interferometer using a narrow band (long coherence length) light source such as a laser could generate the tracking LO. A convenient wavelength for the reference interferometer is at half the wavelength of the OCT light source so that the reference interferometer output would be twice the OCT carrier frequency and could be divided to provide a tracking LO that demodulated the OCT signal directly to DC. Another wavelength could also be used, however.

Another method of preserving the SNR in the case on a nonlinear scan rate is to use the reference signal 208 to drive a phase-locked-loop. This is a closed-loop method similar to those described above, but stability can be higher (at the expense of response speed).

The invention claimed is:

1. An OCT system comprising:
a low coherence source of light for illuminating a sample, wherein the source provides light along a number of incident light paths; and
an interferometer for simultaneously illuminating and collecting light from the sample remitted at several scattering angles, wherein the interferometer includes:
a focusing lens that directs light from such light paths to a common spot of a sample; and
a lens for collimating light from the respective incident light paths and directing such collimated light toward the focusing lens, and for directing scattered light received from the sample by the focusing lens to the respective incident light paths.

2. The OCT system of claim 1 wherein:
the interferometer includes a first beamsplitter that directs light from the source through a delivery fiber optic member for illuminating the sample, and a group of collection fiber optic members arranged relative to the delivery fiber optic member to collect light scatted at respective scattering angles by the sample.

3. The device of claim 2, wherein the fiber optic members are arranged in a bundle.

4. The OCT system of claim 2, further comprising a detector system for detecting light from the group of collection fiber optic members.

5. The OCT system of claim 4, wherein the detector system includes a plurality of detectors, each of the plurality of detectors receiving light from one of the group of collection fiber optic members.

6. The OCT system of claim 5, further comprising an optical delay line.

7. The OCT system of claim 6, wherein a common optical delay line provides light to each of the plurality of detectors.

8. The OCT system of claim 7, wherein respective beamsplitters couple the common delay line and respective collection fibers to respective detectors.

9. The OCT system of claim 1, wherein the interferometer includes:
a first beamsplitter that divides light from the light source and directs the light to at least one delivery fiber member and to a delay line.

10. The OCT system of claim 9, further comprising respective beamsplitters merging light from the delay line with light from the sample through respective collection fibers to respective detectors.

11. The OCT system of claim 9, wherein the interferometer includes a single delivery fiber surrounded by a plurality of collection fibers.

* * * * *

UNITED STATES PATENT AND TRADEMARK OFFICE
CERTIFICATE OF CORRECTION

| | | |
|---|---|---|
| PATENT NO. | : 7,061,622 B2 | Page 1 of 1 |
| APPLICATION NO. | : 10/213326 | |
| DATED | : June 13, 2006 | |
| INVENTOR(S) | : Rollins et al. | |

It is certified that error appears in the above-identified patent and that said Letters Patent is hereby corrected as shown below:

Col. 1, ln. 20, add the following text before "BACKGROUND OF INVENTION":

-- FUNDING   This invention was made with government support under NIH Grant No. EY13015 and NSF Grant No. BES9624617. The government has certain rights in the invention. --

Signed and Sealed this

Twenty-sixth Day of December, 2006

JON W. DUDAS
*Director of the United States Patent and Trademark Office*